(12) United States Patent
Marasco et al.

(10) Patent No.: US 6,479,284 B1
(45) Date of Patent: Nov. 12, 2002

(54) HUMANIZED ANTIBODY AND USES THEREOF

(75) Inventors: Wayne A. Marasco, Wellesley, MA (US); Joyce Lavecchio, Charlestown, MA (US); Abner Mhashilkar, Houston, TX (US); Urban Ramstedt, Boston, MA (US); David Ring, Palo Alto, CA (US); Bridget Eberhardt, Rowley, MA (US); Julie Porter-Brooks, Westford, MA (US)

(73) Assignees: Dana-Farber Cancer Institute, Inc., Boston, MA (US); Avant Immunotherapeutics, Inc., Needham, MA (US); Chiron Corporation, Emeryville, CA (US)

( * ) Notice: Subject to any disclaimer, the term of this patent is extended or adjusted under 35 U.S.C. 154(b) by 0 days.

(21) Appl. No.: 09/660,169

(22) Filed: Sep. 12, 2000

Related U.S. Application Data

(63) Continuation of application No. PCT/US99/05262, filed on Mar. 11, 1999
(60) Provisional application No. 60/077,845, filed on Mar. 13, 1998.

(51) Int. Cl.$^7$ .......................... C12N 5/06; G01N 33/53; C12P 21/04; C07K 16/00
(52) U.S. Cl. ................. 435/339.1; 435/7.1; 435/69.7; 530/388.35
(58) Field of Search .............. 530/388.35; 435/7.1, 435/69.7, 339.1

(56) References Cited

U.S. PATENT DOCUMENTS 5,565,332 A 10/1996 Hoogenboom et al. .... 435/69.1
5,824,307 A 10/1998 Johnson ................... 424/133.1

OTHER PUBLICATIONS

Mhashilkar, A., et al., EMBO J. 14: 1542–1551 (1995).
Mhashilkar, A., et al., J. Virol. 71: 6486–6494 (1997).
Rosok, M., et al., J. Biol. Chem. 271: 22611–22618 (1996).
Baca, M., et al., J. Biol. Chem. 272: 10678–10684 (1997).
Krishnan, I., et al., Cancer 80 (Suppl): 2667–2674 (1997).
Heath, J., et al., Proc. Natl. Acad. Sci. USA 94: 469–474 (1997).
Marken, J., et al., Proc. Natl. Acad. Sci. USA 89: 3503–3507 (1992).
Barre–Sinoussi, et al., Science 220: 868–871 (1983).
Gallo, R., et al., Science 224: 503 (1984).
Gartner, et al., JAMA 256: 2365–2371 (1986).
Koenig, et al., Science 233: 1089–1093 (1986).
Pope, et al., Cell 78: 389–398 (1994).
Weissman, et al., Proc. Nat'l. Acad. Sci. USA 92: 826–830 (1995).
Dalgleish, et al., Nature 312: 763 (1984).
Klatzman, et al., Nature 312: 767 (1984).
Maddon, et al., Cell 47: 333–348 (1986).
McDougal, et al., Science 231: 382 (1986).
Helseth, et al., J. Virol. 64: 6314–6318 (1990).
Kowalski, et al., Science 237: 1351–1355 (1987).
Stein, et al., Cell 49: 659–668 (1987).
Lifson, et al., Nature 323:725 (1986).
Sodroski, et al., Nature 322: 470 (1986).

(List continued on next page.)

*Primary Examiner*—Hankyel T. Park
(74) *Attorney, Agent, or Firm*—Nixon Peabody LLP

(57) ABSTRACT

A humanized antibody framework motif is described. Preferably, the motif is encoded by the $V_H$ gene of K5B8 and the $V_L$ gene of TR1.6. This humanized antibody preferably contains the variable region of a tat antibody.

32 Claims, 13 Drawing Sheets

OTHER PUBLICATIONS

Dayton, A., et al., Cell 44: 941–947 (1986).
Fisher, A., et al., Nature 320: 367–371 (1986).
Kao, S., et al., Nature 330: 489–493 (1987).
Laspia, M., et al., Cell 59: 283–292 (1989).
Feinberg, M., et al., Proc. Natl. Acad. Sci. USA 88: 4045–4049 (1991).
Huang, L., et al., EMBO J. 13: 2886–2896 (1994).
Harrich, D., et al., EMBO J. 16: 1224–1235 (1997).
Cupp, C., et al., Oncogene 8: 2231–2236 (1993).
Viscidi R., et al., Science 246: 1606–1608 (1989).
Howcroft, T., et al., Science 260: 1320–1322 (1993).
Li, C., et al., Proc. Natl. Acad. Sci. USA 92: 5461–5464 (1995).
Westendorp, M., et al., EMBO J. 14: 546–554 (1995).
Sastry, K., et al., J. Biol. Chem. 265, :20091–20093 (1990).
Buonaguro, L., et al., J. Virol. 66: 7159–7167 (1992).
Buonaguro, L., et al., J. Virol 68: 2677–2682 (1994).
Nakajima, K., et al., J. Immunol. 142: 531 (1989).
Scala, G., et al., J. Exp. Med. 179: 961–971 (1994).
Duh, E., et al., Proc. Natl. Acad. Sci. USA 86: 5974–5978 (1989).
Poli, G., et al., J. Exp. Med. 172: 151–158 (1990a).
Poli, G., et al., Proc. Natl. Acad. Sci. USA 87: 782–785 (1990b).
Popik, W., et al., J. Virol. 67: 1094–1099 (1993).
Westendorp, M., et al., J. Virol. 68: 4177–4185 (1994).
Ott, M., et al., Science 275: 1481–1485 (1997).
Li, C., et al., Proc. Natl. Acad. Sci. USA 94: 8116–8120 (1997).
Goldstein, G., Nature Med. 1:960–964 (1996).
Haubrich, R., et al., J. Infect. Dis. 172: 1246–1252 (1995).
Hsu, M., et al., Proc. Natl. Acad. Sci. USA 90: 6395–6399 (1993).
Sullenger, B., et al., Cell 63: 601–608 (1990).
Chang, H., et al., Gene Therapy 1: 208–216 (1994).
Zhou, C., et al., Gene 149: 33–39 (1994).
Aguilar–Cordova, E., et al., Gene Therapy 2: 181–186 (1995).
Vandendriessche, T., et al., J. Virol. 69: 4045–4052 (1995).
Lisziewiez, J., et al., Gene Therapy 7: 2209–2216 (1996).
Rosenzweig, M., et al., J. Virol. 71: 2740–2746 (1997).
Biswas, D., et al., Proc. Natl. Acad. Sci. USA 90: 11044–11048 (1993).
Poznansky, M., et al., Human Gene Therapy 9: 487–496 (1998).
Riddell, S., et al., Nature Med. 2: 216–223 (1996).

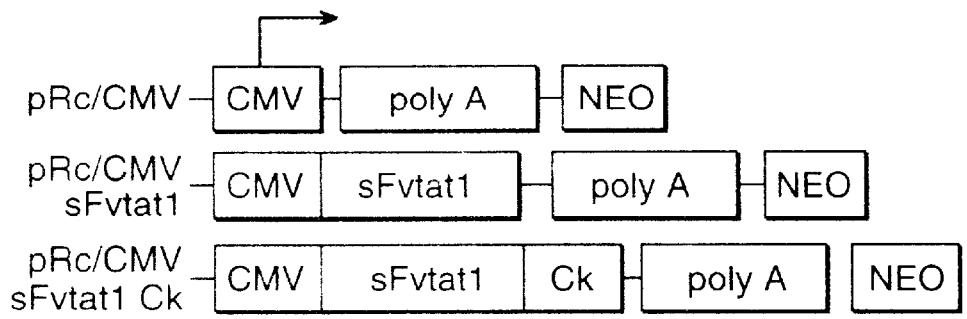
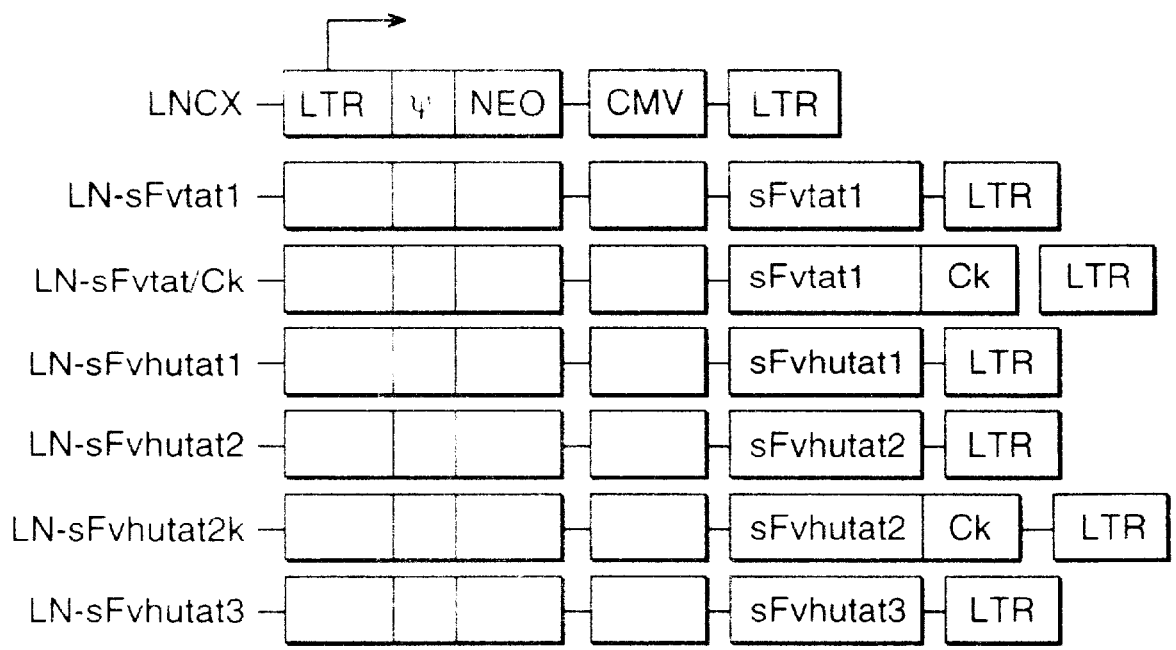
FIG. 1

MEAN FLUORESCENT INTENSITY MEASUREMENTS

| ANTIBODY | NON-TRANSDUCED PBMC | TRANSDUCED PBMC sFvtatICk (MURINE) |
|---|---|---|
| MINUS ANTIBODY | – | – |
| CD2 | +++ | +++ |
| CD3 | ++ | ++ |
| CD4 | + | + |
| CD8 | ++ | ++ |
| CD15 | + | + |
| CD19 | – | – |
| CD28 | + | + |
| CD31 | ++ | + |
| CD58 | ++ | + |
| CD74 | – | + |
| CD80 | + | + |
| CD86 | + | ++ |
| ICAM | ++ | +++ |
| MHC-I | ++++ | +++ |
| MHC-II | ++++ | +++ |
| b2MICROGLOBULIN | ++++ | ++++ |

FIG. 6

FLOW CYTOMETRY ANALYSIS OF NON-TRANSDUCED PBMC'S AND TRANSDUCED PBMC'S (sFvtatICk) USING A PANEL OF CELL SURFACE PHENOTYPE MARKERS. THE TRANSDUCED PBMC'S HAVE BEEN UNDER G418 SELECTION

SCALE:
– 0-10
+ 11-99
++ 100-199
+++ 200-299
++++ <300

HEAVY CHAIN

```
           frm1
sFvtat1    PVKLQESGPGLVAPSQRLSITCTVSGFSLT
sFvhutat1  Q.Q.KQ......H...S............
K5B8       QVQLKQSGPGLVHPSQSLSITCTVSGFSLT
           cdr1      frm2
sFvtat1    SYGVHWVRQPPGKGLEWLV
sFvhutat1  ...........S........
K5B8       SYGVHWVRQSPGKGLEWLG
           cdr2
sFvtat1    VIWSDGSTTYNSALKS
sFvhutat1  ................
K5B8       VMWRGGSTDYNAAFMS
           frm3
sFvtat1    RLNISKDNSKSQVFLKMNSLQTDDTAMYYCAR
sFvhutat1  ....T.....R...F.........A....I...
K5B8       RLNITKDNSKAQVFFKMNSLQADDTAIYYCAK
           cdr3          frm4
sFvtat1    EPPTTYV..CLLGQGTSVTVSS
sFvhutat1  ...........|..........
K5B8       SMITTGFVMDSWGQGTSVTVSS
```

LIGHT CHAIN

```
           frm1
sFvtat1    ELVLTQSPLSLPVSLGDHASISC
sFvhutat1  ...M........TP.EP......
TR1.6      ELVMTQSPLSLPVTPGEPASISC
           cdr1
sFvtat1    RSSQSLVHSNGITYLH
sFvhutat1  ................
TR1.6      RSSQSLLHGNGYNYLD
           frm2                cdr2
sFvtat1    WYLQKPGQSPKLLIYKVSNRFS
sFvhutat1  ..........Q...........
TR1.6      WYLQKPGQSPQLLIYLGSNRAS
           frm3
sFvtat1    GFPDRFSGSGSGTDFTLKIGRVEAEDLGVYFC
sFvhutat1  ........................S......V....
TR1.6      GVPDRFSGSGSGTDFTLKISRVEAEDVGVYYC
           cdr3       frm4
sFvtat1    SQSTHIPWTFGGGTKLEIKRA
sFvhutat1  ...........Q.........
TR1.6      MQALQPPYTFGQGTKL-----
```

FIG. 7

HUMANIZED ANTIBODY AND USES THEREOF

This application is a continuation of copending international application PCT/US99/05262, filed Mar. 11, 1999, which is hereby incorporated by reference, and which designated the U.S. The nonprovisional application designated above, namely application PCT/US99/05262, filed Mar. 11, 1999, claims the benefit of U.S. provisional application No. 60/077,845, filed Mar. 13, 1998.

This work was supported in part by NIH grants P30 AI28691 (Center for AIDS Research), P30 CA06516 (Cancer Center Grant), AI28785, AI33802, AI34753 and the U.S. government has certain rights thereto.

FIELD OF THE INVENTION

The present invention is directed to a humanized single chain antibody having a framework motif, preferably a motif containing no murine amino acids, that result in the humanized antibody having activity comparable to the corresponding murine antibody. Preferably, the antibody is a Tat antibody.

BACKGROUND OF THE INVENTION

Human immunodeficiency viruses type 1 and type 2 (HIV-1 and HIV-2) are the etiologic agents of acquired immunodeficiency syndrome (AIDS) in humans (Barre-Sinoussi et aL., 1984). AIDS results from the depletion of CD4-positive T lymphocytes in HIV-infected individuals (Fauci et al., 1984).

HIV-1 infects T lymphocytes, monocytes/macrophage, dendritic cells and, in the central nervous system, microglia (Gartner et al., 1986; Koenig et al., 1986; Pope et al., 1994; Weissman et al., 1995). All of these cells express the CD4 glycoprotein, which serves as the receptor for HIV-1 and HIV-2 (Dalgleish et al., 1984; Klatzman et al., 1984; Maddon et al., 1986). Efficient entry of HIV-1 into target cells is dependent upon binding of the viral exterior envelope glycoprotein, gp120, to the CD4-amino-terminal domain (McDougal et al., 1986; Helseth et al., 1990). After virus binding, the HIV-1 envelope glycoproteins mediate the fusion of viral and host cell membranes to complete the entry process (Kowalski et al., 1987; Stein et al., 1987; Helseth et al., 1990). Membrane fusion directed by HIV-1 envelope glycoproteins expressed on the infected cell surface leads to fusion with uninfected CD4-positive cells, resulting in syncytia (Lifson et al., 1986; Sodroski et al., 1986). HIV-1 and HIV-2 contain numerous regulatory proteins including tat, rev, nef, vpu/vpx and vpr in addition to pol, gag and the envelope glycoproteins.

Tat, a 16 kD regulatory protein, is expressed early in the viral life cycle and is absolutely required for viral replications[1,2]. Tat acts as a potent transcriptional activator of viral gene expression through its binding to a RNA stem-loop structure called the transactivation response element (TAR) that is located 40 bp downstream from the site of initiation of transcription in the 5' long terminal repeat (LTR). Tat functions primarily to stimulate transcription initiation and increase transcriptional elongation[3,4,5]. However, new evidence suggests that Tat may also be required for efficient HIV-1 reverse transcription[6,7].

Apart from its role in viral replication, Tat protein also has an effect on cellular genes that may aid in the dissemination of virus infection. For example, Tat has been implicated in several immunosuppressive effects including increasing the expression of the potent immunosuppressive cytokine transforming growth factor β1 (TGF-β1)[8], suppressing antigen-induced proliferation of T cells[9] and decreasing the activity of an MHC class I gene promoter, thereby providing a mechanism whereby HIV-1-infected cells may be able to avoid immune surveillance and recognition of specific cytotoxic T lymphocytes[10]. Other cellular genes such as those involved in G1 checkpoint control, p53 and in cellular defense against oxidative stress, Mn-superoxide dismutase are also downregulated by Tat[11,12].

Tat has additional functions in the pathogenesis of AIDS, in part because of its ability to be released from HIV-1-infected cells through a non-classical secretory pathway and to enter the nuclei of both infected and uninfected cells. Tat uptake not only enhances HIV-1 transcription in infected cells, it also affects a range of host cellular genes in both infected and uninfected cells. This includes activation of cellular genes such as tumor necrosis factor (TNF) α and β[13,14,15] and IL-6[16,17], which in turn may activate HIV-1 gene expression and replication leading to further spread of HIV-1[18,19,20,21]. Tat has also been shown to upregulate IL2 secretion in ctivated T cells[22] and to recapitulate the phenotype of increased IL-2 secretion in response to costimulation with CD3 plus CD28 that is seen in HIV-1-infected primary T-cells that are stimulated via CD3 and CD28 receptors[23]. Extracellular Tat has been shown to activate uninfected quiescent T cells in vitro and in vivo, thereby causing uninfected cells to become highly permissive to productive HIV-1-infection[24]. In this way, Tat protein is unique among the HIV-1 proteins in not only being critical for ‚iral transcriptional activation but also for its role in evolvinga self-perpetuating mechanism to actively generate cells permissive to productive and cytopathic infection[24,25].

Consequently Tat is likely to have both direct and indirect effects in the pathogenesis of AIDS through its multiple roles in the HIV-1 life cycle and on the immune system. It would be desirable to have more efficient means for disrupting Tat interactions. Disruption of Tat protein interaction with TAR RNA or the cellular factors that bind Tat protein, and of Tat protein release from HIV-1-infected cells, thus represents an important target for pharmacologically and genetically based therapeutic interventions to combat HIV-1 infection. While clinical results with the Tat antagonist Ro24-7429 showed no evidence of anti-viral activity[26] despite prolonged inhibition of HIV-1 replication in vitro[27], the results of a number of Tat directed in vitro gene therapy studies have been encouraging[28,29,30,31,32,33,34], particularly when combined with pharmacologic inhibitors of NF-kB[35,36].

A murine anti-tat sFv antibody, which is directed intracellularly against the proline-rich N-terminal activation domain of HIV-1 Tat and hence sometimes referred to as an intrabody, is a potent inhibitor of Tat-mediated LTR transactivation and HIV-1 infection[36,37,38]. However, murine antibodies can produce undesired immune responses which can reduce or totally abolish the effectiveness of the antibody. The immune response can also cause undesired side effects. In order to minimize evoking an immune response against the murine anti-tat sFv or transgene encoding it in a clinical setting[39], CDR grafting experiments were performed to completely humanize the murine anti-tat sFv. Unfortunately, "humanizing" an antibody is not as efficient a process as sometimes presented. Compatible human framework regions must be chosen from heavy chain and light chain sequences of over 1000 human sequences each. However, the resulting antibody despite having the same variable region as the murine antibody frequently does not have the same effectiveness as the original murine antibody. Frequently the "humanized" antibody will retain some "murine" amino acid residues. It would be desirable to have a framework motif that produces an antibody having a protective efficiency comparable to the murine antibody.

SUMMARY OF THE INVENTION

We have now discovered a framework motif that produces a humanized antibody such as an anti-tat sFv intrabody that demonstrated a level of activity, e.g., anti-HIV-1 activity that was comparable to that of the parental murine sFv.

The preferred sequence was completely human, retaining none of the murine amino acids. The comparable human heavy chain and light chain are selected. One preferred framework motif is based upon the human $V_H$ gene K5B8 and $V_L$ gene TR1.6.

While the sequence is preferably completely humanized, some murine amino acid residues can be retained. The amino acid sequences encoded by these genes are aligned against the murine sequence to determine where the amino acids differ. One humanized antibody retains at least one of the murine amino acid residues at the FRM2/CDR2 border and the FRM3/CDR3 border of the heavy chain. In another embodiment, at least one murine amino acid within the FRM3 sequence of the light chain is also retained. Preferred positions are the first murine amino acid within FRM3 after the CDR2 border that differs from the human sequence and the last such amino acid within FRM3 before the CDR border. In yet another embodiment, at least three of the four murine positions described above are maintained. For example, all four of these murine amino acids are retained. In another embodiment the murine amino acid at the heavy chain CDR3/FR4 boundary is also maintained. This murine amino acid can be maintained with any of the above-described combination of murine and human amino acids. However, most preferably, the framework motif retains none of the murine sequences.

We have found, for example, that a humanized test antibody retaining no murine amino acids demonstrated a level of HIV-1 protective activity comparable to the parent murine sFv when transduced PBMC expressing the murine or humanized sFv antibodies were challenged with HIV isolates. In contrast, a humanized version retaining five of the murine amino acids and one retaining the murine amino acid at the heavy chain CDR3/FR4 boundary while demonstrating some level of protective activity do not demonstrate comparable protective activity.

These antibodies can be used in a variety of ways. For example, the DNA encoding such an antibody can be used to transform a cell which will then express the antibody intracellularly. For example, when the leader sequence is removed the antibody will not go to the endoplasmic reticulum (ER). In one embodiment the appropriate nuclear localization sequence is added, and the antibody can target a protein at a specific location intracellularly and prevent binding. In another embodiment, a protein such as the tat protein, can be targeted. in the cytoplasm by deleting the leader sequence without adding a nuclear localization sequence.

For example, the antibody sFvtat1Ck, a murine anti-tat sFv intrabody, directed against the proline rich N-terminal activation domain of HIV-1, is a potent inhibitor of HIV-1 replication (*EMBO J.* 14:1542, 1995). Stably transfected CD4 SupT1 cells expressing this intrabody were resistant to HIV-1 infection at high m.o.i. with both the laboratory isolate HxB2 and six syncytium inducing (SI)-primary isolates. Persistently infected U1 cells, which can be induced to increase HIV-1 mRNA synthesis upon addition of Phorbol 12-myristate 13 acetate (PMA), which is equal to 12-0-Tetradecanoylphorbyl β-acetate (TPA), or Tumor necrosis factor-alpha (TNFα), showed decreased production of HIV-1 in the presence of sFvtat1 Ck. In transduced CD4+-selected, CD8+-depleted and total PMBCs, the sFvtat1Ck expressing cells showed marked inhibition of HIV-1 replication. A humanized antibody prepared,by substituting compatible human framework regions chosen from a large database of human $V_H$ and $V_L$ sequences on the basis of high overall framework matching, similar CDR length and minimal mismatching of canonical and $V_H/V_L$ contact residues altered as taught, sFvhutnat2, demonstrated a level of anti-HIV-1 activity that was comparable to the parental murine sFv when transduced PBMCs expressing the murine or humanized sFv intrabodies were challenged with HxB2 and two SI-primary isolates. However, as mentioned above, the other humanized antibody did not display such activity.

These antibodies can also be used extracellularly to target Tat. The antibodies can also be used to bind to Tat and when combined with a detectable moiety used to measure levels of Tat. The Tat levels can be used diagnostically and/or prognostically.

BRIEF DESCRIPTION OF THE FIGURES

FIG. 1 is a schematic representation of a variety of anti-tat sFv intrabody expression vectors. sFvtat1 and murine antibody sFvtat1Ck were cloned into pRc/CMV (Invitrogen). sFvtat1, sFvtat1Ck, and the humanized versions sFvhutat1, sFvhutat2, sFvhutat2Ck, sFvhutat3, were cloned into the retroviral vector pLNCX. All the constructs were confirmed by DNA sequencing. Empty vectors pRc/CMV and LNCX were used as negative controls throughout the studies.

FIG. 6 shows FACS analysis of PBMCs and transduced PBMCs expressing the sFvtat1Ck intrabody.

FIG. 7 shows the construction of a three humanized anti-tat sFv intrabodies. Illustration showing amino acid sequences used for generating sFvhutat intrabodies. Human $V_H$ gene K5B8 and $V_L$ gene TR1.6 were used for humanization procedures. The upper panel illustrates the heavy chain sequence comparisons and changes (SEQ ID NO:1 shows the amino acid of humanized sFvtat2 (sometimes sFvhutat_); SEQ ID NO:2 shows the amino acid sequence encoded by K5B8), and the lower panel shows the light chain sequence comparisons and changes (SEQ ID NO:3 shows the amino acid of sFvtat2 ; SEQ ID NO:4 show the amino acid sequence encoded by TR1.6). Shaded boxes contain framework amino acids that are different between the murine and human genes. The completely humanized version, sFvhutat2, was made by changing all murine framework amino acids in both heavy and light chains to the corresponding human sequences. In the second humanized version, sFvhutat1, murine amino acids were retained at three heavy chain and two light chain framework positions. In the third humanized version, sFvhutat3, only a single murine amino acid was retained at the heavy chain CDR3/FR4 boundary. The sFvhutat1version was further modified by adding a complete human $C_{kappa}$ sequence at its C-terminal.

Figure 8A:
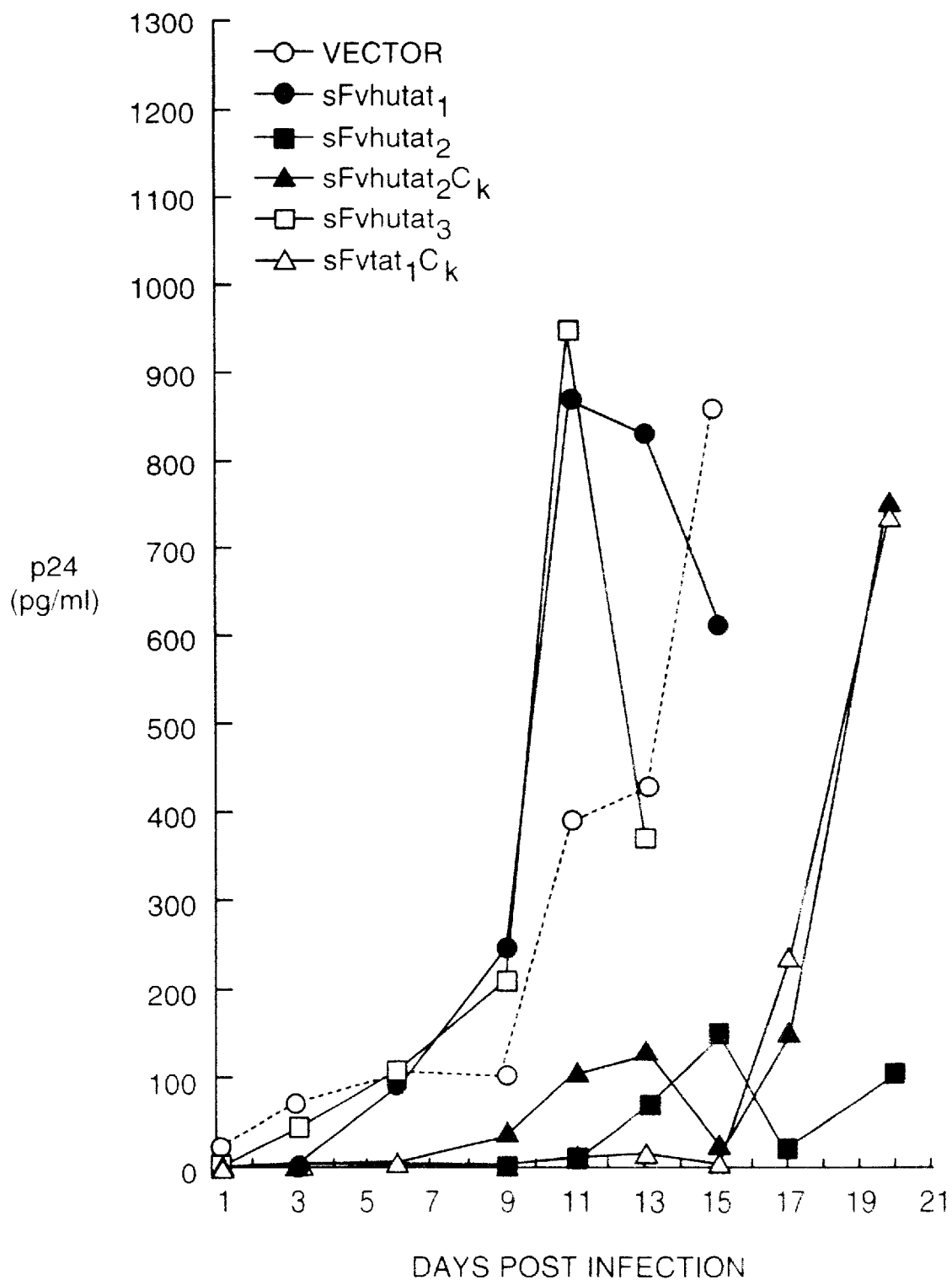
Figure 8B:
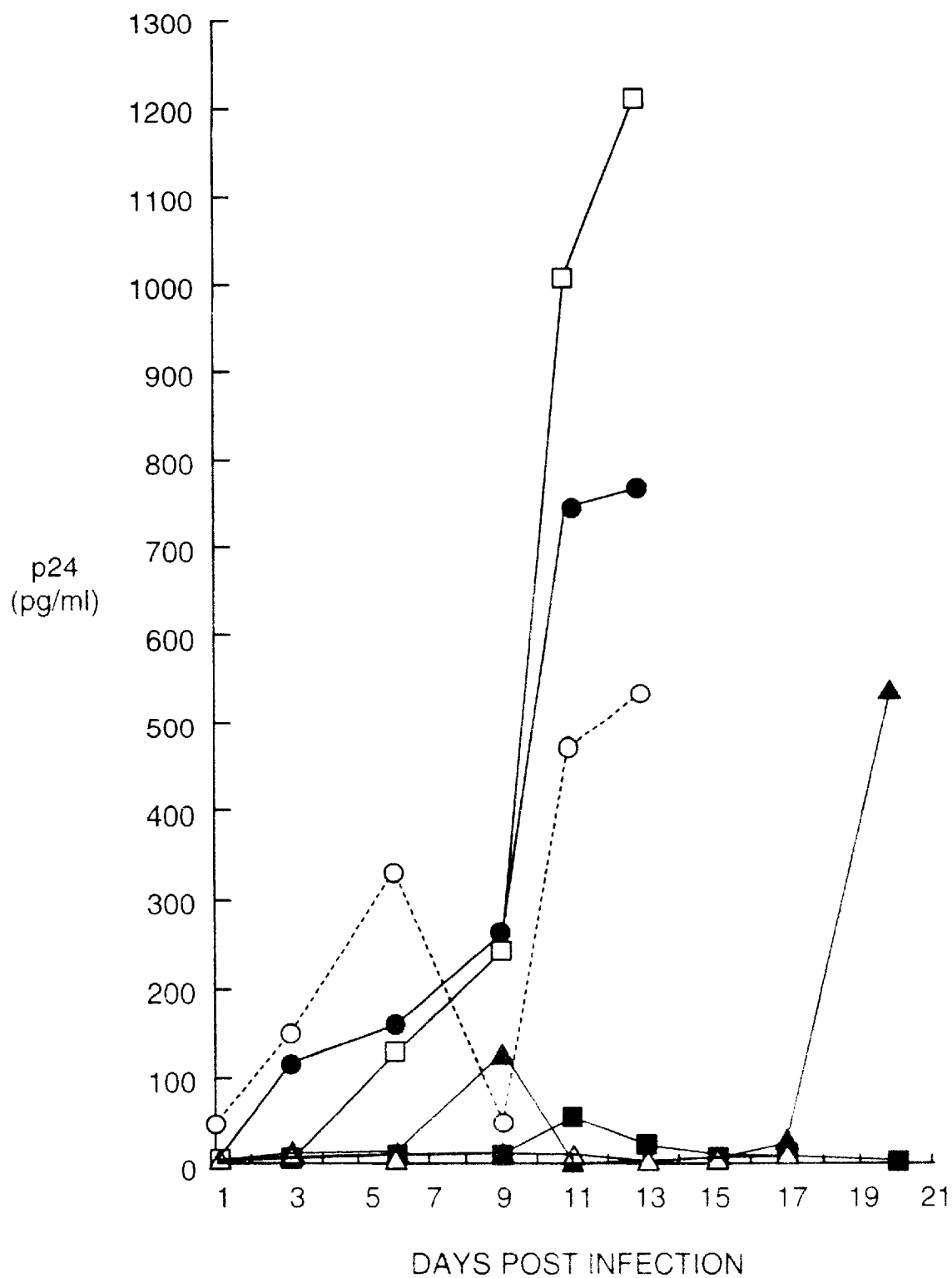
Figure 8C:
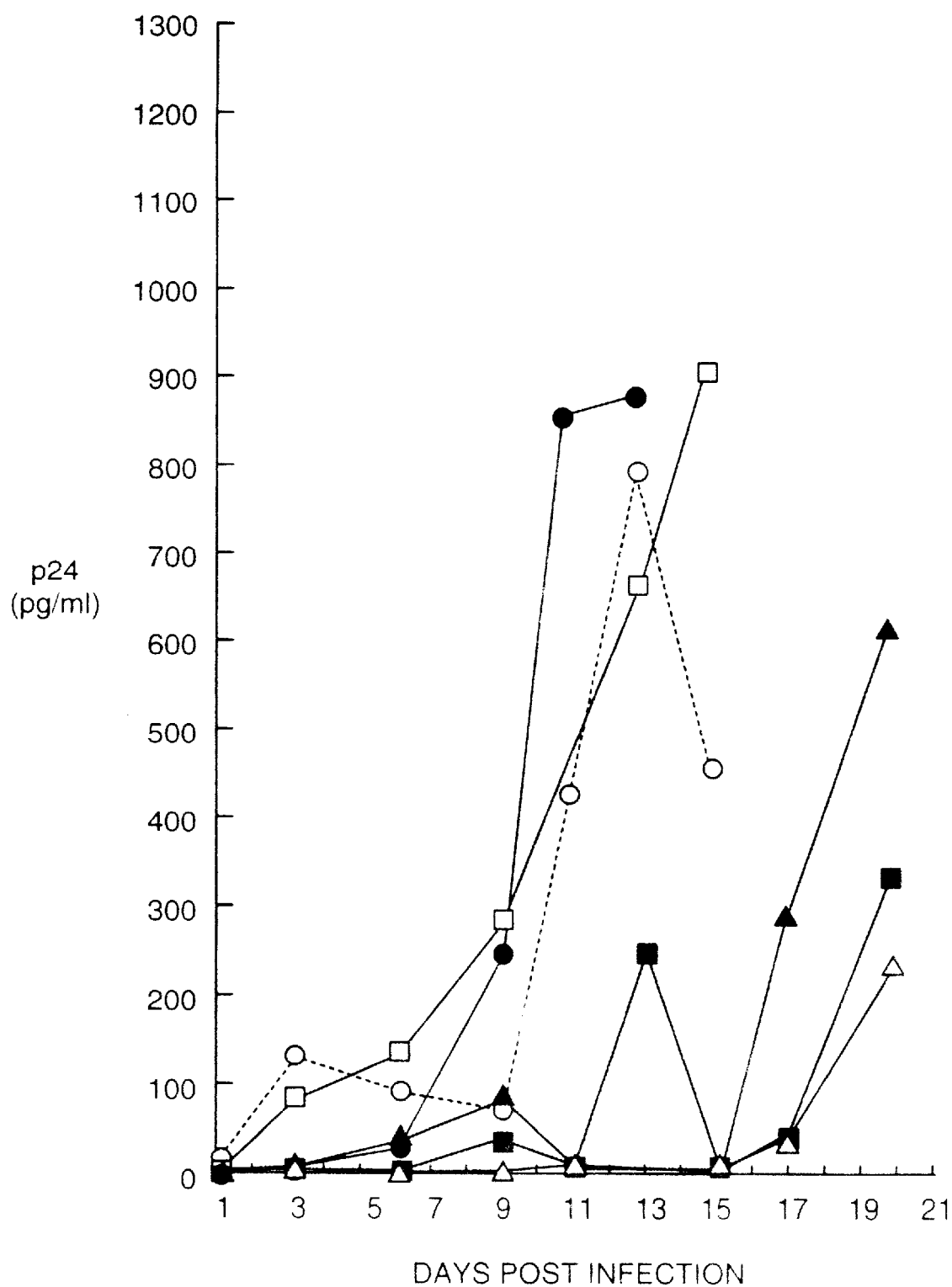

FIGS. 8A–8C show resistance of anti-tat sFv intrabody transduced PBMCs to laboratory isolate HxB2 (FIG. 8A, m.o.i.=0.1), SI-primary isolate #1 (FIG. 8B, m.o.i.=0.05) and SI-primary isolate #2 (FIG. 8C, m.o.i.=0.05). Transduced PBMCs ($10^6$/mL) were infected with HIV-1 for 4 hours and then replaced with fresh culture media. (open circles), vector; (closed circles), sFvhutat1; (closed squares), sFvhutat2 ; (closed triangles), sFvhutat2 Ck; (open squares), sFvhutat3; and (open triangles), murine sFvtat1Ck. Viral particles in culture medium were measured by using an p24 gag Elisa kit according to manufacturer's instructions.

Figure 9:
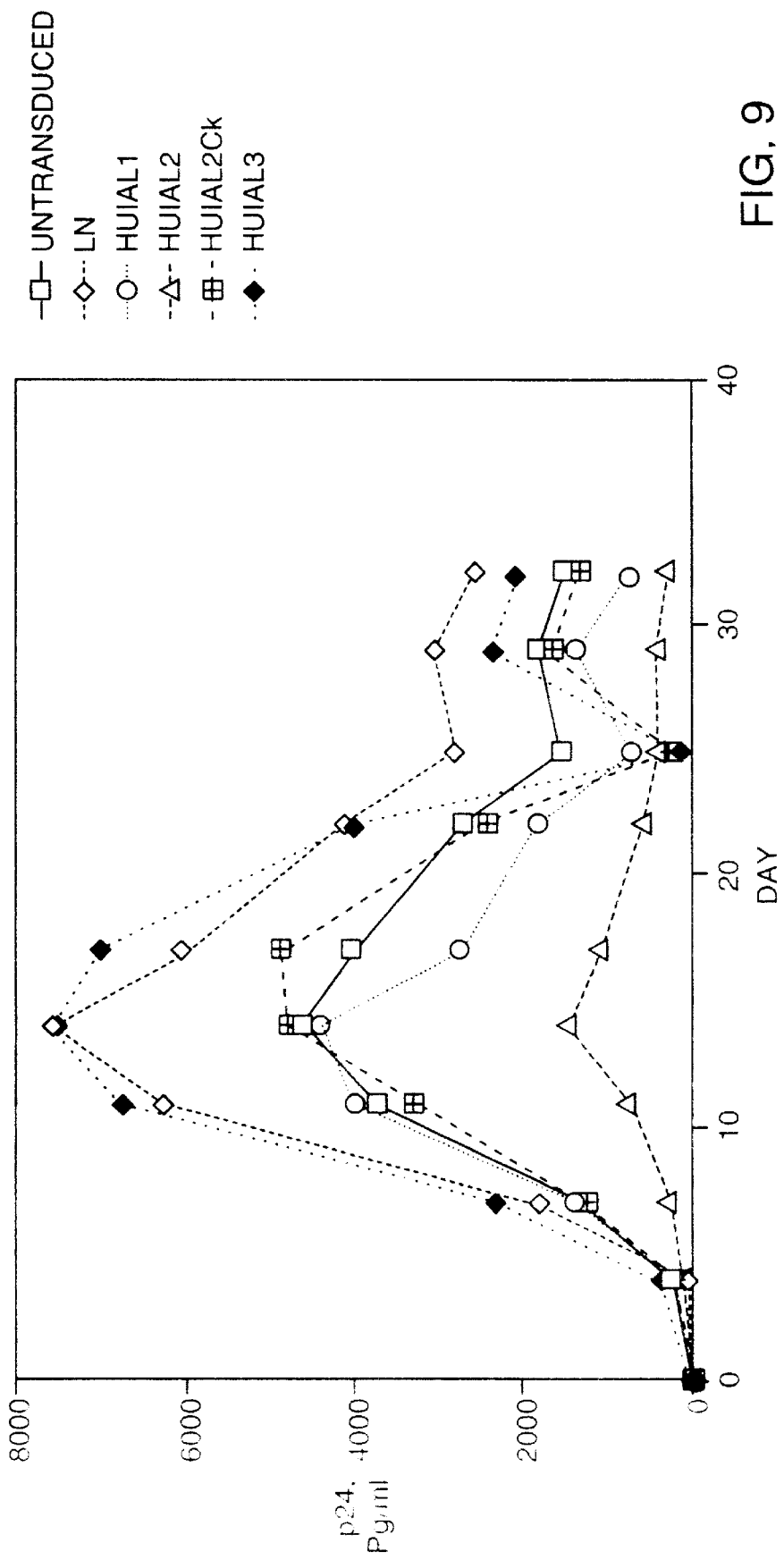

FIG. 9 shows protection by sFvhutat2 in transduced human peripheral blood lymphocytes. The PBMC were challenged with HIV-1 HxBc2 at m.o.i.=0.05.

DETAILED DESCRIPTION OF THE INVENTION

We have now discovered a framework motif that produces a humanized antibody such as an anti-tat sFv intrabody that demonstrated a level of activity, e.g., anti-HIV-1 activity that was comparable to that of the parental murine sFv.

By retaining no murine amino acids in the "humanized" framework one is able to obtain a more effective antibody. The comparable human heavy chain and light chain are selected. For example, the human $V_H$ gene K5B8 and $V_L$ gene TR1.6. The amino acid sequences encoded by these genes are then aligned against the murine sequence to determine where the amino acids differ. In one embodiment, some murine amino acid sequences may be retained. While such humanized antibodies are closer to the murine antibody, they surprisingly did not demonstrate a comparable protective activity, although they do demonstrate some protection. For example, one retains at least one of the murine amino acid residues at the FRM2/CDR2 border and the FRM3/CDR3 border of the heavy chain. In another example, at least one murine amino acid within the FRM3 sequence of the light chain is also retained. As used herein, a murine amino acid is used to refer to the situation where the murine and human sequence differ. For instance, positions are the first murine amino acid within FRM3 after the CDR2 border that differs from the human sequence and the last such amino acid within FRM3before the CDR border. In one embodiment. at least three of the four murine positions described above are maintained. For example, all four of these murine amino acids are retained. In another embodiment the murine amino acid at the heavy chain CDR3/FR4 boundary is also maintained. This murine amino acid can be maintained with any of the above-described combination of murine and human amino acids.

We have found, however, that it was a humanized test antibody retaining no murine amino acids that demonstrated a level of activity against HIV-1 comparable to the parent murine sFv when transduced PBMC expressing the murine or humanized sFv antibodies were challenged with HIV isolates.

Most preferably the framework region is used with the variable region of a Tat antibody. For example, one directed against the proline rich N-terminal activation domain of HIV-1 Tat. The variable region can be obtained from any type of antibody e.g., a murine antibody.

Antibodies can be prepared by means well known in the art. The term "antibodies" is meant to include monoclonal antibodies, polyclonal antibodies and antibodies prepared by recombinant nucleic acid techniques that are selectively reactive with a desired antigen such as Tat. The term "selectively reactive" refers to those antibodies that react with one or more antigenic determinants of the desired antigen, e.g., Tat, and do not react with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes.

For example, antibodies may be raised against amino-terminal (N-terminal) or carboxyl-terminal (C-terminal) peptides of a polypeptide. Most preferably, one selects the N-terminal activation domain of HIV-1 Tat.

One method is by using hybridoma mRNA or splenic mRNA as a template for PCR amplification of such genes [Huse, et al., *Science* 246:1276 (1989)]. For example, intrabodies can be derived from murine monoclonal hybridomas [Richardson J. H., et al., *Proc Natl Acad Sci USA* 92:3137–3141 (1995); Biocca S., et al., *Biochem and Biophys Res Comm,* 197:422–427 (1993) Mhashilkar, A. M., et al., *EMBO J* 14:1542–1551 (1995)]. These hybridomas provide a reliable source of well-characterized reagents for the construction of antibodies and are particularly useful when their epitope reactivity and affinity has been previously characterized. Another source for such construction includes the use of human monoclonal antibody producing cell lines. [Marasco, W. A., et al., *Proc Natl Acad Sci USA,* 90:7889–7893 (1993); Chen, S. Y., et al., *Proc Natl Acad Sci USA* 91:5932–5936 (1994)]. Another example includes the use of antibody phage display technology to construct new antibodies against different epitopes on a target molecule. (Burton, D. R., et al., *Proc Natl Acad Sci USA* 88:10134–10137 (1991); Hoogenboom H. R., et al., *Immu-* nol Rev 130:41–68 (1992); Winter G., et al., *Annu Rev Immunol* 12:433–455 (1994); Marks, J. D., et al., *J Biol Chem* 267: 1600–16010 (1992); Nissim, A., et al., *EMBO J* 13:692–698 (1994); Vaughan T. J., et al., *Nature Bio* 14:309–314 (1996); Marks C., et al., *New Eng J Med* 335:730–733 (1996)]. For example, verye large naive human sFv libraries have been and can be created to offer a large source or rearranged antibody genes against a plethora of target molecules. Smaller libraries can be constructed from individuals with autoimmune [Portolano S., et al., *J Immunol* 151:2839–2851 (1993); Barbas S. M., et al., *Proc Natl Acad Sci USA* 92:2529–2533 (1995)] or infectious diseases [Barbas C. F., et al., *Proc Natl Acad Sci USA* 89:9339–9343 (1992); Zebedee S. L., et al., *Proc NatlAcad Sci USA* 89:3175–3179 (1992)] in order to isolate disease specific antibodies.

Other sources include transgenic mice that contain a human immunoglobulin locus instead of the corresponding mouse locus as well as stable hybridomas that secrete human antigen-specific antibodies. [Lonberg, N., et al., *Nature* 368:856–859 (1994); Green, L. L., et al., *Nat Genet* 7:13–21 (1994)]. Such transgenic animals provide another source of human antibody genes through either conventional hybridoma technology or in combination with phage display technology. In vitro procedures to manipulate the affinity and fine specificity of the antigen binding site have been reported including repertoire cloning [Clackson, T., et al., *Nature* 352:624–628 (1991); Marks, J. D., et al., *J Mol Biol* 222:581–597 (1991); Griffiths,. A. D., et al., *EMBO J* 12:725–734 (1993)], in vitro affinity maturation [Marks, J. D., et al., *Biotech* 10:779–783 (1992); Gram H., et al., *Proc Natl Acad Sci USA* 89:3576–3580 (1992)], semi-synthetic libraries (Hoogenboom. H. R., supra; Barbas, C. F., supra; Akamatsu, Y., et al., *J Immunol* 151:4631–4659 (1993)] and guided selection [Jespers, L. S., et al., *Bio Tech* 12:899–903 (1994)]. Starting materials for these recombinant DNA based strategies include RNA from mouse spleens [Clackson, T., supra] and human peripheral blood lymphocytes [Portolano, S., et al., supra; Barbas, C. F., et al., supra; Marks, J. D., et al., supra; Barbas, C. F., et al., *Proc Natl Acad Sci USA* 88:.7978–7982 (1991)] and lymphoid organs and bone marrow from HIV-1-infected donors [Burton, D. R., et al., supra; Barbas, C. F., etal., *Proc NatlAcad Sci USA* 89:9339–9343 (1992)].

Thus, one can readily screen an antibody to insure that it has a sufficient binding affinity for the antigen of interest. The binding affinity ($K_d$) should be at least about $10^{-7}$ l/mol, more preferably at least about $10^{-8}$ l/mol.

For example, cDNA clone encoding Tat or a fragment thereof may be expressed in a host using standard techniques such that 5–20% of the total protein that can be recovered from the host is the desired protein. Recovered proteins can be electrophoresed using PAGE and the appropriate protein band can be cut out of the gel. The desired protein sample can then be eluted from the gel slice and prepared for immunization. Alternatively, a protein of interest can be purified by using conventional methods such as, for example, ion exchange hydrophobic, size exclusion, or affinity chromatography.

Once the protein immunogen is prepared, mice can be immunized twice intraperitoneally with approximately 50 micrograms of protein immunogen per mouse. Sera from such immunized mice can be tested for antibody activity by immunohistology or immunocytology on any host system expressing such polypeptide and by ELISA with the expressed polypeptide. For immunohistology, active antibodies of the present invention can be identified using a biotin-.conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active antibodies according to the invention can be sacrificed three days later and their spleens removed for fusion and hybridoma production. Positive supernatants of such. hybridomas can be identified using the assays described above and by, for example, Western blot analysis.

To further improve the likelihood of producing an antibody, the amino acid sequence of polypeptides encoded by a eukaryotic nucleotide sequence of the present invention may be analyzed in order to identify portions of amino acid sequence which may be associated with increased immunogenicity. For example, polypeptide sequences may be subjected to computer analysis to identify potentially immunogenic surface epitopes. Such computer analysis can include generating plots of antigenic index, hydrophilicity, structural features such as amphophilic helices or amphophilic sheets and the like.

For preparation of monoclonal antibodies directed toward polypeptides encoded by a eukaryotic nucleotide sequence of the invention, any technique that provides for the production of antibody molecules by continuous cell lines may be used. For example, the hybridoma technique originally developed by Kohler and Milstein (*Nature* 256:495–497, (1973)), as well as the trioma technique, the human B-cell hybridoma technique (Kozbor et al., *Immunology Today*, 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al. U.S. Pat. Nos. 4,704,694 and 4,976,778).

Another method for preparing antibodies is by in vitro immunization techniques, such as using spleen cells, e.g., a culture of murine spleen cells, injecting an antigen, and then screening for an antibody produced to said antigen. With this method, as little as 0.1 micrograms of antigen can be used, although about 1 microgram/milliliter is preferred. For in vitro immunization, spleen cells are harvested, for example, mice spleen cells, and incubated at the desired amount, for example, $1 \times 10^7$ cells/milliliter, in medium plus with the desired antigen at a concentration typically around 1 microgram/milliliter. Thereafter, one of several adjuvants depending upon the results of the filter immunoplaque assay are added to the cell culture. These adjuvants include N-acetylmuramyl-L-alanyl-D-isoglutamine [Boss, *Methods in Enzymology* 121:27–33 (1986)], Salmonella typhimurium mitogen [Technical Bulletin, Ribi ImmunoChem. Res. Inc., Hamilton, Mont.] or T-cell condition which can be produced by conventional techniques [See, Borrebaeck, C. A. K., *Mol. Immunol.* 21:841–845 (1984); Borrebaeck, C. A. K., *J. Immunol.* 136:3710–3715 (1986)] or obtained commercially, for example, from Hannah Biologics, Inc. or Ribi ImmunoChem. Research Inc. The spleen cells are incubated with the antigen for four days and then harvested.

Single cell suspensions of the in tatro immunized mouse spleen cells are then incubated, for example on antigen-nitrocellulose membranes in microfilter plates, such as those available from Millipore Corp. The antibodies produced are detected by using a label for the antibodies such as horse-radish peroxidase-labeled second antibody, such as rabbit anti-mouse IgA, IgG, and IgM. In determining the isotype of the secreted antibodies, biotinylated rabbit anti-mouse heavy chain specific antibodies, such as from Zymed Lab., Inc. can be used followed by a horseradish peroxidase-avidin reagent, such as that available from Vector Lab.

The insoluble products of the enzymatic reaction are visualized as blue plaques on the membrane. These plaques are counted, for example, by using 25 times magnification. Nitrocellulose membrane of the microfilter plaques readily absorb a variety of antigens and the filtration unit used for the washing step is preferred because it facilitates the plaque assay.

One then screens the antibodies by standard techniques to find antibodies of interest. Cultures containing the antibodies of interest are grown and induced and the supernatants passed through a filter, for example, a 0.45 micromiter filter and then through a column, for example, an antigen affinity column or an anti-tag peptide column. The binding affinity is tested using a mini gel filtration technique. See, for example, Niedel, J., *Biol. Chem.* 256:9295 (1981). One can also use a second assay such as a radioimmunoassay using magnetic beads coupled with, for example, anti-rabbit IgG to separate free $^{125}$I-labeled antigen from $^{125}$I-labeled antigen bound by rabbit anti-tag peptide antibody. In a preferred alternative one can measure "on" rates and "off" rates using, for example, a biosensor-based analytical system such as "BIAcore" from Pharmacia Biosensor AB [See, *Nature* 361:186–187 (1993)].

This latter technique requires less antigen than the in vivo immunization because the in vivo method typically requires about 50 micrograms of antigen per mouse per injection and there are usually two boosts following primary immunization for the in vivo method.

Alternatively, one can use a known antibody to the target protein. Thereafter, a gene to at least the antigen binding portion of the antibody is synthesized as described below. As described briefly above, in some preferred embodiments it will also encode an intracellular localization sequence such as one for the endoplasmic reticulum, nucleus, nucleolar, etc. When expression in the ER normal antibody secretory system such as the endoplasmic reticulum-golgi apparatus is desired, a leader sequence should be used. for other locations it should not be present.

Antibody genes can be prepared based upon the present disclosure by using known techniques.

Using any of these antibodies, one can construct $V_H$ and $V_L$ genes. For instance, one can create $V_H$ and $V_L$ libraries from murine spleen cells that have been immunized either by the above-described in vitro immunization technique or by conventional in UiUo immunization and from hybridoma cell lines that have already been produced or are commercially available. One can also use commercially available $V_H$ and $V_L$ libraries. One method involves using the spleen cells to obtain mRNA which is used to synthesize cDNA. Double stranded cDNA can be made by using PCR to amplify the variable region with a degenative N terminal V region primer and a J region primer or with $V_H$ family specific primers, e.g., mouse-12, human-7.

For example, the genes of the $V_H$ and $V_L$ domains of the desired antibody such as one to Tat can be clone and sequenced. The first strand cDNA can be synthesized from, for example, total RNA by using oligo dT priming and the Moloney murine leukemia virus reverse transcriptase according to known procedures. This first strand cDNA is then used to perform PCR reactions. One would use typical PCR conditions, for example, 25 to 30 cycles using e.g. Vent polymerase to amplify the cDNA of the immunoglobulin genes. DNA sequence analysis is then performed. [Sanger, et al., *Proc. Natl. Acad. Sci. USA* 79:5463–5467 (1977)].

Both heavy chain primer pairs and light chain primer pairs can be produced by this methodology. One preferably inserts convenient restriction sites into the primers to make cloning easier.

Thereafter, the variable region is chosen. This is then added to the "humanized" framework motif by standard techniques.

Those of ordinary skill in the art will recognize that a large variety of possible moieties can be coupled to the resultant antibodies or to other molecules of the invention. See, for example, "Conjugate Vaccines", Contributions to Microbiology and Immunology, J. M. Cruse and R. E. Lewis, Jr (eds), Carger Press, New York, (1989), the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myasthenia Gravis by toxin-acetylcholine receptor conjugates." *Jour. Immun.* 133:1335–2549; Jansen, F. K., H. E. Blythman, D. Carriere, P. Casella, 0. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity" . *Immunological Reviews* 62:185–216; and Vitetta et al., supra).

Preferred linkers are described in the literature. See, for example, Ramakrishnan, S. et al., *Cancer Res.* 44:201–208 (1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Antibodies of the present invention can be detected by appropriate assays, e.g., conventional types of immunoassays. For example, a sandwich assay can be performed in which Tat or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured, the amount of the label detected serving as a measure of the amount of anti-urea transporter antibody present in the sample. These and other immunoassays can be easily performed by those of ordinary skill in the art.

The resultant antibody can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector [Geller, A. I. et al., *J. Neurochem*, 64:487 (1995); Lim, F., et al., in DNA Cloning: *Mammalian Systems,* D. Glover, Ed. (Oxford Univ. Press, Oxford England) (1995); Geller, A. I. et al., *Proc Natl. Acad. Sci.:* U.S.A. 90:7603 (1993); Geller, A. I., et al., *Proc Natl. Acad. Sci USA* 87:1149 (1990)], Adenovirus Vectors [LeGal LaSalle et al., *Science,* 259:988 (1993); Davidson, et al., *Nat. Genet* 3:219 (1993); Yang, et al., *J. Virol.* 69:2004 (1995)] and Adeno-associated Virus Vectors [Kaplitt, M. G.. et al., *Nat. Genet.* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofecton, cell microinjection, and viral vectors.

The vector can be employed to target essentially any desired target cell, such as a glioma. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell (Bobo et al., *Proc. Natl. Acad. Sci. USA* 91:2076–2080 (1994); Morrison et al., *Am. J. Physiol.* 266:292–305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of Tat in a sample.

The antibody can also be used to try to bind to and disrupt Tat interaction. For example, in one preferred method the antibody is expressed intracellularly and is used to protect the cell from the presence of Tat by preventing Tat transactivation.

Tat is not present in the endoplasmic relocation (ER) or golgi apparatus. When the target is not in the ER or golgi apparatus, the gene does not encode a functional leader sequence for the variable chains, as it is preferable that the antibody does not encode a leader sequence. The nucleotides coding for such binding portion of the antibody preferably do not encode the antibody's secretory sequences (i.e. the sequences that cause the antibody to be secreted from the cell). One preferred method is set forth in the examples.

The antibody cassette is delivered to the cell by any of the known means. One preferred.delivery system is described in U.S. patent application Ser. No. 08/199,070 by Marasco filed Feb. 22, 1994 and PCT application Ser. No. PCT/US95/ 02140, filed Feb. 21, 1995, which is incorporated herein by reference. This discloses the use of a fusion protein comprising a target moiety and a binding moiety. The target moiety brings the vector to the cell, while the binding moiety carries the antibody cassette. Other methods include, for example, Miller, A. D., *Nature* 357:455–460 (1992); Anderson, W. F., *Science* 256:808–813 (1992); Wu, et al, *J of Biol. Chem.* 263:14621–14624 (1988). For example, a cassette containing these antibody genes, such as the sFv gene, can be targeted to a particular cell by a number of techniques. In the discussion below we will discuss the sFv gene coding for Tat antibodies, which would be preferably introduced into human $CD4^+$ cells. Other delivery methods include the use of microcatheters, for example, delivering the vector in a solution which facilitates transfection, gene gun, naked DNA, adjuvant assisted DNA, liposomes, pox virus, herpes virus, adeno virus, retroviruses, etc.

Preferably the vectors of the present invention use internal ribosome entry site (IRES) sequences to force expression. As disclosed in application Ser. No. 60/005,359, filed Oct. 16, 1995, and PCT application Ser. No. PCT/US96/16531, filed Oct. 16, 1996 the use of IRES allows the "forced-expression" of the desired gene, for example, an sFv. In another embodiment, one can use an IRES to force a stoichiometric expression of light chain and heavy chain. This forced expression avoids the problem of "silencing" where cells expressing the desired protein are phenotypically not seen, which may occur with a wide range of gene products. Another embodiment comprises using the IRES sequences the single chain intrabodies to the IRM of interest can be linked with a selectable marker. Selectable markers are well known in the art, e.g., genes that express protein that change the sensitivity of a cell to stimuli such as a nutrient, an antibiotic, etc. Examples of these genes include neo puro, tk, multiple drug resistance (MDR), etc.

The resultant products of that IRES linkage are not fusion proteins, and they exhibit their normal biological function. Accordingly, the use of these vectors permits the forced expression of a desired protein.

We tested the protective effect of stable expression of the murine sFvtat1Ck intrabody on HIV-1 replication in both acutely infected and persistently infected $CD4^+$ cells. Stably transfected $CD4^+$ SupT1 cells were resistant to HIV-1 infection at high m.o.i. with both the laboratory isolate HxB2 and six SI-primary isolates. Persistently infected U1 cells, which can be induced by PMA and TNFα to significantly increase HIV-1 mRNA synthesis, showed decreased production of HIV-1 in the presence of the anti-tat sFv intrabody. In transduced $CD4^+$-selected, CD8+-depleted and total PMBCs, the murine sFvtat1Ck expressing cells showed marked inhibition of HIV-1 replication. We have shown that an antibody humanized by the present method produced comparable results. When transduced PBMCs expressing the murine sFvtat1Ck or the humanized sFvhutat2 and sFvhutat2Ck intrabodies were challenged with HxB2 and two SI-primary isolates, comparable levels of inhibition of HIV-1 inhibition were observed. However, in contrast to our observations with murine sFvtat1, the addition of a $C_{kappa}$ domain to sFvhutat2 did not consistently improve its antiviral activity thus raising the possibility that framework residues on murine sFvtat1 may be responsible for mediating this $C_{kappa}$ effect. Two humanized antibodies that differed, sFvtat1 (sometimes sFvha tat1) and sFutat3 (sometimes sFuhu3) did not produce these results. Both these antibodies retained murine amino acids in the antibody framework, five and one, respectively. In determining whether the humanized antibody has comparable activity to the murine antibody one can measure for any of a number of functions. Preferably, one measures for an activity for the purpose one is using the antibody for. For example the murine tat antibody displays an anti-HIV infection activity as determined by looking at delay in $p^{24}$ production in cells, e.g., PBMC, challenged with HIV isolates. Comparable activity means the humanized antibody shows at least about 75% of the activity of the murine antibody, more preferably at least about 80% activity, still more preferably at least about 85% activity, even more preferably at least about 90% activity. Yet more preferably, the humanized antibody should display at least about 95% of the activity of the murine antibody in such a test.

Intracellular immunization strategies that are aimed at inhibiting target gene expression can be RNA (antisense, ribozymes, RNA decoys) or protein (intrabodies, dominant-negative mutants) based and each group of inhibitors has advantages and limitations. While RNA based strategies are often limited by the inability to achieve high levels of inhibitor expression or to allow accurate subcellular localization, protein based strategies may be limited by their potential immunogenicity, particularly when the genetic strategy is to treat a chronic infection such as AIDS. Like its normal cellular protein counterparts, the intracellularly expressed protein transgene will be degraded by the proteasome and presented on the cell surface by MHC-I to antigen presenting cells[44,45]. When the MHC-I presented peptides are recognized as foreign, a subsequent cellular immune response can be elicited against the transduced cells. Indeed, while results of several cancer gene therapy marking studies[46,47] and gene replacement studies[48,49] that have used the neomycin selection marker have shown persistence of the marker gene and a HIV-1 revM10 based intracellular immunization study has shown preferential survival of the revM10 expressing cells compared to the non-expressing frameshift revM10 transduced cells[50], there is growing evidence that a CTL response can limit long term protein transgene expression[39]. Because of these considerations, humanization of a murine antibody is important. However, it must be done in a manner that does not adversely affect efficacy.

For example, the anti-tat sFv was humanized by substituting compatible human framework regions that were chosen from a database of over twelve hundred human $V_H$ sequences and over one thousand $V_L$ sequences. Best matched human $V_H$ and $V_L$ sequences were chosen on the basis of high overall framework matching, similar CDR length, and minimal mismatching of canonical and $V_H/V_L$ contact residues. The humanized construct, sFvhutat2, contained completely human frameworks. Two alternative sequences were also constructed. In sFvhutat1, murine amino acids were retained at three heavy chain and two light chain framework positions. In sFvhutat3, only a single murine amino acid was retained at the heavy chain CDR4/FR4 boundary. Our results show that sFvhutat1with no murine framework residues retained, was as active as the original murine sFvtat1Ck in several assays, while the two other humanized versions, which were closer to the protectively active murine antibody, sFvhutat1and sFvhutat3were considerably less protective. The unusual W→L substitution at the first heavy chain framework 4 residue of murine sFvtat 1 seems most likely (based on DNA sequence not shown) to have resulted from paired single base deletion/insertion events such that the leucine in question is actually coded by the last base of the last CDR codon and the first two bases of the first framework 4 codon.

Recent advances in anti-retroviral therapies have been coupled with the encouraging results of clinical studies of HIV-1-infected individuals that are being treated with highly active anti-retroviral therapy (HAART)[51] (sometimes referred to as triple anti-HIV-1 drug therapy). However, an increasing number of patients who initially had profound anti-viral responses to HAART are now experiencing recurrence of plasma viremia[52;53]. Furthermore, a reservoir of latently infected cells persists in these HIV-1-infected individuals[42,43]. As shown in FIG. 4, anti-tat sFv intrabody gene therapy can inhibit HIV-1 replication in a transduced population of latently infected cells. Indeed, in this patient population, the genetic inhibition of Tat protein function combined with pharmacologic inhibitors of HIV-1 reverse transcriptase and protease may represent a powerful and important adjuvant therapy to inhibit the development of multiple drug resistant viruses in these patients. Recent report that pharmacologic inhibitors of NF-kB combined with anti-tat sFv intrabody gene therapy resulted in more durable inhibition of HIV-1 replication than did treatment with either inhibitor alone suggests that a combined pharmacologic and genetic strategy may improve the survival of transduced cells and prolong clinical benefit in a gene therapy setting[36].

The introduction into susceptible cells of a humanized anti-tat sFv intrabody that interferes with viral replication represents an attractive approach to the treatment of HIV-1 infection. For example, using CD4+ mononuclear cells from HIV-1-infected patients successfully transduced with retroviral vectors to express the anti-tat sFv intrabody with an intrabody active against a wide range of primary isolates. The data presented in FIG. 3, combined with our recent studies which demonstrate that transduced and sFvtat1Ck expressing CD4+-selected mononuclear cells from HIV-1-infected patients at different stages of disease can be protected and expanded in culture[38] indicates that the humanized sFvhutat2 will be active against a wide range of primary isolates and against the quasi-species of HIV-1 that are commonly found within HIV-1-infected individuals with advanced disease. Furthermore, the N-terminal epitope to which the anti-tat sFv intrabody is directed is highly conserved[25]. Viruses that have escaped sFvtat1Ck intrabody suppression were used to challenge freshly transduced cells, and the viruses remained sensitive to sFvtat1Ck suppression, indicating that limitations are more a matter of the long term level of transgene expression in vivo rather than due to the development of anti-tat sFv intrabody escape mutants (Mhashilkar[37], and data not shown).

The critical role that the Tat protein plays both directly and indirectly in the pathogenesis of AIDS through its multiple roles in the HIV-1 life cycle and on the immune system suggest that it is a preferred target for the gene therapy of HIV-1- infection and AIDS. A role of Tat protein in HIV-1 related malignancies[54,55,56,57,58] and in upregulating other viral promoters[59,60,61] has also been proposed. Using a humanization motif as taught here through CDR grafting results in an anti-tat sFv antibody that can be directed against the same critical epitope of Tat protein and maintains potent anti-viral activity. These studies form the basis of a future clinical gene therapy trial in which both the protective effect(s) of the sFvhutat2 intrabody on CD8+-depleted, transduced PBMCs and the development of CTL activity against the intrabody expressing cells will be examined in HIV-1-infected individuals with advanced disease.

Another preferred embodiment of this invention is in the diagnosis of susceptibility to HIV infection. This can be accomplished by using the antibody to measure for the presence of tat. Increased levels of tat protein are indicative of enhanced susceptibility to HIV.

Using any suitable technique known in the art, such as Northern blotting, quantitative PCR, etc. the level of a protein, e.g., tat, can be used to measure levels of e.g. its RNA expression. Methods for using antibodies to detect the presence of a protein are known to those skilled in the art. They include, for example, conjugating the antibody to a detectable marker.

Alternatively, the antibodies of the invention can be used in standard techniques such as Western blotting to detect the presence of cells expressing tat, to quantify the level of expression.

EXAMPLES

Stable Cell Lines and Primary Cell Cultures

Stable clones of $CD4^+$-SupT1 cells expressing the murine anti-tat sFv intrabody sFvtatICk (SupT-sFvtat1Ck cells) or pRc/CMV (Invitrogen) vector (SupT-vector cells) have been previously described[36,37]. Persistently HIV-1 infected U1 pro-monocytic cells[42,43] ($2\times10^6$ cells) were transfected with DEAE-dextran using 10–14 ug pRc/CMV vector, pRc/CMV-sFvtat1, pRc/CMV-sFvtat1Ck or pRc/CMV-sFvTac (leaderless sFv directed against the human interleukin-2 receptor) and were incubated at 37° C. in RPMI media. 48 hours post-transfection, the cells were exposed to selection media with 500 μg/ml G418. Six to eight days later, the bulk stable cells were thoroughly washed with PBS and exposed to different concentrations of PMA (0–10 ng/ml) or TNFα (0–20 μg/ml) for four-to-five hours at 37° C. The cells were then washed and supernatants were collected on alternate days and analyzed for p24 antigen.

SupT1 cells, U1 cells and PBMCs were grown in RPMI 1640 medium supplemented with 10% FCS. The PE501 ecotropic cell line and PG13 amphotropic retrovirus producing packaging cell lines were maintained in Dulbecco's modified Eagle's medium (DMEM) supplemented with 10% FCS (Gibco-BRL). The same culture conditions were used for NIH3T3cells and COS-1 cells. All cells were grown at 37° C in a humidified incubator with 5% $C0_2$.

Preparation of HIV-1 Primary Isolate Stocks

For the preparation of virus stocks, $10–15\times10^6$ cells, either SupT1 or MT4 (for laboratory isolates) or 1 μg/ml PHA activated PBMCs (for primary isolates) in six to eight ml PRMI media were challenged with 50–60 ng p24 (or in some cases 100,000 to 120,000 cpm RT). The panel of European syncytium-inducing (SI)-primary isolates used in these studies were screened for their ability to infect SupT 1 cells (a gift from Dr. Jan Albert, Karolinska Institute, Stockholm, Sweden) but were passages only in PBMCs. The cells were incubated at 37° C. until post-infection days seven to nine and then centrifuged at 2000 rpm for 20 min at 4° C. The supernatants were removed and transferred to another tube and centrifuged again at 3000 rpm for 15 minutes at 4° C. The supernatants were then filtered through a 0.45 um filter and aliquoted. Virus titers ($TCID_{50}$/ml) were determined with H9 cells by analysis of cyopathic effects as previously described[62]. HIV-1 Challenge Experiments with Stably Transfected SupT-sFvtat1Ck Cells.

Stable clones of SupT-sFvtat1Ck and SupT-vector cells ($2\times10^6$ cells/six ml RPMI media) were challenged with six European SI primary isolates (20 ng p24/ml) for four hours at 37° C. and then washed once with RPMI medium and resuspended in six ml of medium. Every two-three days post-challenge, five ml of supernatant was removed and replenished with new medium of equal volume. The supernatants were analyzed for p24 levels using a radioimmunoassay kit for the HIV-1 p24 Gag protein (DuPont) according to manufacturer's instructions. Briefly, the supernatants were inactivated with 5% Triton X-100 and then incubated with anti-p24 antibody (2 hours at room temperature) followed by an overnight incubation (room temperature) with $^{125}$-I Tracer. The samples were then incubated with second antibody, centrifuged and the resulting pellet was counted on a gamma-counter. The p24 levels were calculated using a standard curve generated with a kit viral lysate stock solution. For studies that analyzed the effect of HIV-1 challenge dose (FIG. 2), the same protocol was used except that the challenge dose was 25 ng, 250 ng and 2500 ng p24.

Establishment of Retrovirus Producing Packaging Cell Lines

The different anti-tat sFv intrabody genes were cloned into the LNCX MuLV shuttle vector under. the control of the CMVIE promoter[63]. The empty LNCX or LN-anti-tat sFv intrabody vectors (10 μg) were transfected by calcium phosphate into the ecotropic cell line PE501 ($10^6$ cells/100 mm dishes)[63]. Twelve hours later, the cells were washed with PBS and three ml of fresh medium was added to the cells. After an additional 24 hours, the supernatants from the transfected cells were collected, cleared by low speed centrifugation (3000×g; 1200 rpm), filtered through a 0.45 um filter and three ml was used to infect the amphotropic packaging cell line, PG13 ($10^6$ cells/100 mm dish) in the presence of 8 μg/ml protamine sulfate. 48 hours post-infection, the cells were washed and treated with selection medium containing 800 μg/ml G418. Once producer cell lines were established, confluent monolayer cells were split and fresh medium was added. The cells were then incubated at 32° C., retroviral containing supernatants were harvested, filtered and analyzed for viral titers by titration on COS-1 cells. Viral titers of $10^{-5}$ to $10^{-6}$ infectious particles/ml for individual subclones were routinely obtained. Anti-tat sFv intrabody expression in the stable PG13 packaging cell lines was confirmed by radioimmunoprecipitation (data not shown).

Transduction of PBMCs and CD4+ Mononuclear Cells

Peripheral blood mononuclear cells (PBMCs) were isolated by Ficoll-hypaque density centrifugation (Pharmacia, Sweden). Cells were stimulated for 60–70 hours at $1 \times 10^6$ cells/ml with 1 μg/ml PHA (Murex Diagnostics Limited, England) and 20 U/ml IL-2 (Collaborative Research, Bedford, Mass.) or in some experiments with 5 ng/ml anti-human CD3, 5 ng/ml anti-human CD28 and 20 U/ml IL-2 (FIG. 8). In some studies, cells were either $CD4^+$-selected or $CD8^+$-depleted. $CD4^+$-selected cells were obtained by incubation of $20 \times 10^6$ PBMCs on $CD4^+$- coated Selector flasks (AIS, Santa Clara, Calif.) for one hour at room temperature. Following incubation, flasks were washed 6× with PBS ($Ca^{++}$ and $Mg^{++}$ free). After the washes, four ml of RPMI supplemented with 10%FCS, P/S, 1 μg/ml PHA and 100 U IL-2 was added to the flask and incubated at 37° C. and 5% $CO_2$ for 60–70 hours. To obtain the $CD8^+$-depleted cells, $20 \times 10^6$ PBMCs were incubated on $CD8^+$-selector flasks (AIS, Santa Clara, Calif.) for one hour at room temperature. Following incubation, the supernatant was removed from the flask and centrifuged for 10 minutes at 1200 rpm. The cell pellet was resuspended in four ml of RPMI supplemented with 10%FCS, P/S 1 μg/ml PHA and 100 U IL-2 and placed into a T25 tissue culture flask and incubated at 37° C. and 5% $CO_2$ for 60–70 hours.

Transductions were performed on three consecutive days. The cells were washed and,placed in an RPMI phosphate free medium supplemented with 10% dialyzed FCS (Gibco, Grand Island, N.Y.) for six hours at 37° C. Cells were washed, resuspended in complete RPMI medium and mixed with retroviral supernatant to obtain a final MOI of 1.0 in the presence of 8 αg/ml protamine sulfate (Sigma, St. Louis, Mo.). The cells were centrifuged for one hour at (1000×g; 2600 rpm) at 32° C. The cells were then incubated overnight at 32° C.[64]. This procedure was repeated for two more consecutive days. Following this incubation, the cells were washed with fresh medium and resuspended in medium supplemented with 20 U/ml IL-2 and 800 μg/ml G418 and incubated at 37° C. The medium was changed on day five with continued G418 selection. After 10 days in culture, the cells were washed and stimulated with irradiated human PBMCs (5000 Rads) at a ratio of 1:10 (transduced cells: feeders) and 1 μg/rnl PHA. Four days later the cells were fed with medium supplemented with 20 U/ml IL-2 and 800 μg/ml G418. When cells started to expand (circa day 10–14) they were washed and prepared for HIV-1 challenge.

Transduction efficiency of the PBMCs was determined by PCR-amplification with appropriate primers of the neomycin gene[65]. Twenty four hours after the last transduction, 20,000 cells were collected and PCR band intensity was compared to the intensity of a quantitation curve. The transduction efficiency was estimated to be around 10–15%.

HIV-1 Challenge of Transduced PBMCs and CD4+- Mononuclear Cells.

For the PBMC and CD4+mononuclear cell challenge experiments, cells were incubated in six well plates containing $1 \times 10^6$ cells/three ml of medium. Cells were incubated for four hours or in some cases overnight at 37° C. with HIV-1 challenge doses of MOI 0.1–0.5. The cells were then washed and resuspended in 3 ml of fresh medium. Every two to three days, two ml of supernatants were collected for p24 assay and replaced pith the same volume of fresh medium.

FACS Analysis of PBMCs

Cells (transduced PBMCs and non-transduced PBMCs) were washed 2× with PBS supplemented with 20% fetal calf serum (PBS/2%FCS) and resuspended at $4 \times 10^6$ cells/ml. 50 μl of cell suspension ($2 \times 10^6$ cells) were used for each antibody staining. Cells were pipetted into 12×75 polystyrene round bottom tubes (Falcon). 1 μl of antibody in 50 μl of PBS/2%FCS was added to the appropriate tube and incubated for 1 hour at 4° C. Following incubation, the cells were washed 3× with 1 ml/tube of PBS/FCS, (1200 rpm for 3minutes). After the washes were completed, 50 μl of a 1:50 dilution of the secondary antibody (FITC-labeled goat anti-mouse IgG) was added to the appropriate tubes and incubated for 30 minutes at 4° C. Following incubation, the cells were washed 3× with 1 ml/tube of PBS/FCS, (1200 rpm for three minutes). Cell pellets were resuspended in 500 μl PBS/FCS and analyzed by Becton-Dickinson FACsSCAN flow cytometer (San Jose, Calif.). The MAbs were obtained from the following sources; Becton-Dickinson: mouse anti-human CD4, mouse anti-human CD8, mouse anti-human CD15, mouse anti-human CD19; Endogen: mouse anti-human CD2 , mouse anti-human CD31, mouse anti-human ICAM; Immunotech: mouse anti-human CD3, mouse anti-human CD28, mouse anti-human MHC-I, mouse anti-human β2 microglobulin: Biosource: mouse anti-human CD58, mouse anti-human MHC-II; Ancell: mouse anti-human CD74, mouse anti-human CD80, mouse anti-human CD86; Sigma: goat anti-mouse FITC. Construction of Humanized Anti-Tat sFv Intrabodies.

The anti-tat sFv was humanized by substituting compatible human framework regions chosen from a database constructed in MicroSoft Excel 5. The database contained 1287 human $V_H$ sequences and 1041 human $V_L$ sequences downloaded from Andrew C. R. Martin's KabatMan web page (http://www.biochem.ucl.ac.uk/~martin/abs/simkab.html) or obtained by sequencing of human antibody V region clones at Chiron Corporation. The anti-tat $V_H$ and $V_L$ amino acid sequences were aligned and mismatched residues were highlighted and scored using Excel macros. "Best matched" human $V_H$ and $V_L$ sequences for anti-tat were chosen on the basis of high overall framework matching, similar CDR length. and minimal mismatching of canonical and $V_H/V_L$ contact residues. Framework sequences from these matches were then concatenated with CDR sequences from murine anti-tat to design humanized anti-tat heavy and light chain sequences.

DNA fragments encoding desired humanized sequences were constructed by the PCR approach of Jayaraman[66]. Sets of complementary single stranded oligonucleotides of 39 to 69 bases were synthesized with staggered overlaps that could be annealed to create the desired fragments. Sixteen oligonucleotides (eight pairs) were used to generate each heavy chain sequence followed by a (Gly₄Ser)₃ linker, and 12 oligonucleotides (six pairs) were used to generate each light chain sequence. The oligonucleotides for each fragment were mixed and annealed, then amplified by PCR using a terminal oligonucleotide from each fragment as primer. The heavy chain/linker fragment was spliced to the light chain fragment via a Sacd site incorporated into the first two codons of the light chain, and the completed humanized constructs were transferred into expression vectors using flanking restriction sites.

Results
Dose Dependent Inhibition of HIV-1 Replication in Stably Transfected CD4⁺ SupT Cells Expressing the sFvtat1Ck Intrabody The anti-tat sFv intrabody genes used in this study are depicted in FIG. 1. The parent genes $V_H$ and $V_L$ are derived from the hybridoma cell line 1D9D5 that produces a murine MAb directed against the proline rich N-terminal activation domain of HIV-1 tat to produce the anti-tat sFv intrabody, termed sFvtat1[37].

Figure 2A:
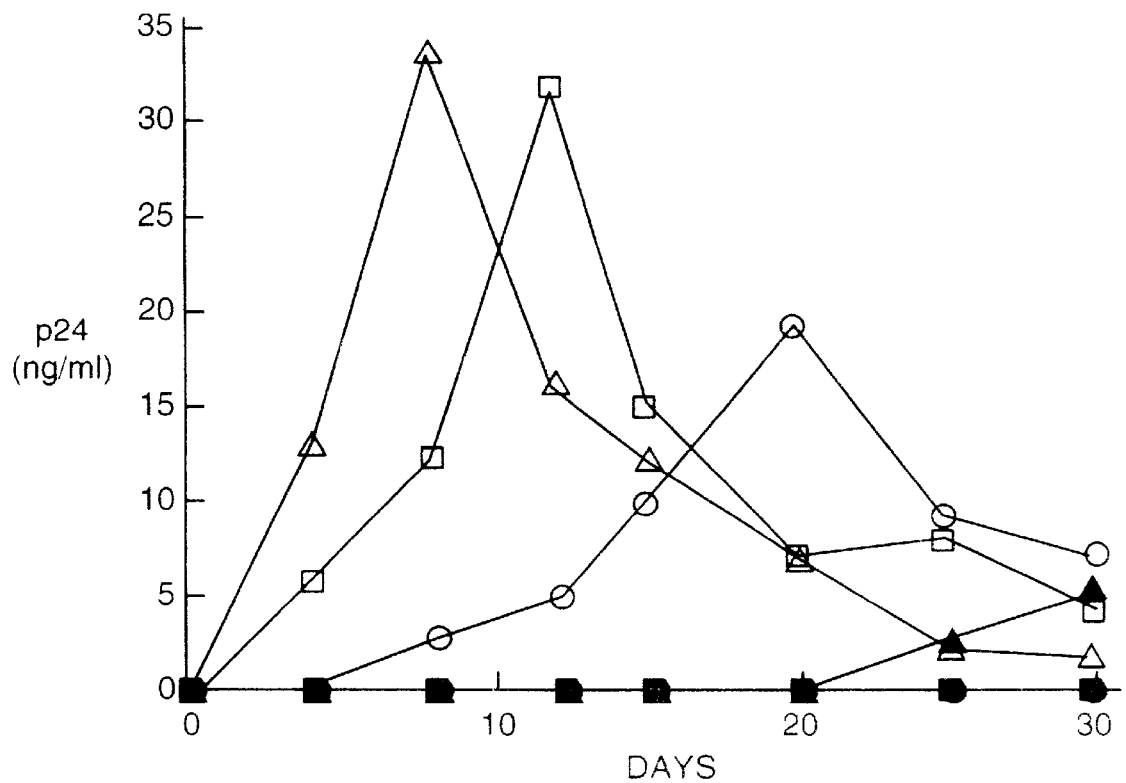
FIGS. 2A and 2B show the effects of HIV-1 challenge dose on resistance of sFvtat1Ck-expressing cells to HIV-1 infection. Stably transfected SupT1-sFvtatICk and SupT-vector cell clones were challenged with different amounts of either HIV-1$_{HxB2}$(FIG. 2A) or European SI-primary isolate #1 (FIG. 2B). Open symbols (SupT-vector cells) or closed symbols (SupT-sFvtat1Ck cells) were challenged with different multiplicity of infection (m.o.i.) HIV-1. Circles, m.o.i.=0.075 and 0.062; squares, m.o.i.=0.75 and 0.62; triangles, m.o.i.=7.5 and 6.2 for HxB2 and SI-primary isolate #1, respectively. The cell free supernatant samples obtained on different days post-infection were analyzed for p24 using a commercial RIA kit (DuPont).

The addition of the human $C_{kppa}$ domain (i.e., the constant domain of a human kappa light chain) to produce the murine anti-tat sFv-human $C_{kappa}$ intrabody, termed sFvtat1Ck, results in a more potent inhibitor of HIV-1 replication than sFvtat 1 presumably due to $C_{kappa}$-induced intrabody dimerization[37,38]. The effect of HIV-1 challenge dose on this sFvtat1Ck-mediated protection was not reported. Stably transfected SupT-sFvtat1Ck cells were challenged with different amounts of HIV-1 to determine the effect of HIV-1 challenge dose on the degree of inhibition of HIV-1 replication. As shown in FIG. 2A, SupT-vector cells challenged with the laboratory strain HIV-1$_{HxB2}$ (sometimes HIV-1 IIIB (HxB2)) showed a progressively earlier and higher level of p24 production as the challenge dose was increased over a 100-fold range. In contrast, with SupT-sFvtat1Ck, only the highest challenge dose of HIV-1$_{III-B}$ resulted in detectable p24 production and this was delayed until day 25. Inhibition of Replication of Syncytium-Inducing (SI) Primary Isolates in SupTsFvtat1Ck Cells.

Figure 2B:
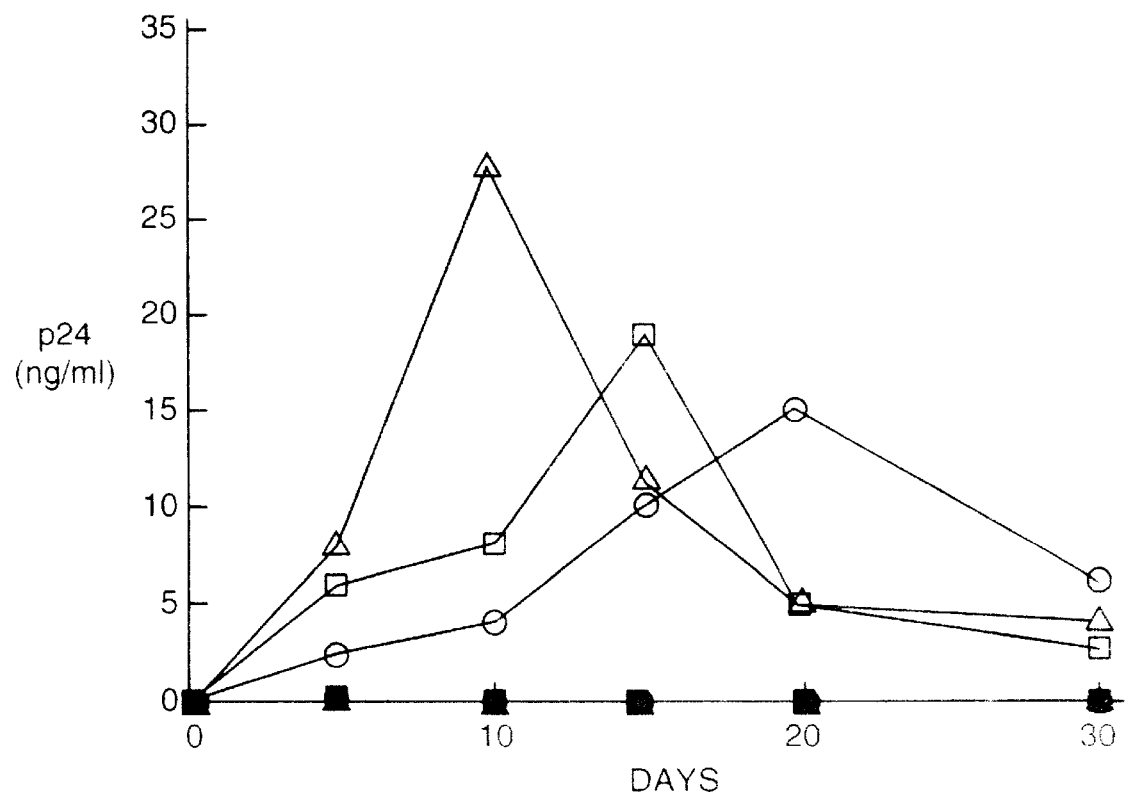

A panel of syncytium-inducing primary isolates were screened for their ability to infect SupT1 cells and were subsequently used in HIV-1 challenge experiments. Similar to the results described above and as shown in FIG. 2B, when SupT-(murine)sFvtat1Ck or control SupT-vector cells were challenged with primary isolate #1, the SupT-vector cells again demonstrate a progressively earlier and higher level of p24 production as the challenge dose was increased over a 100-fold range. Over the time course of this experiment, p24 production remained undetectable in the SupT-sFvtat1Ck cell cultures.

Figure 3:
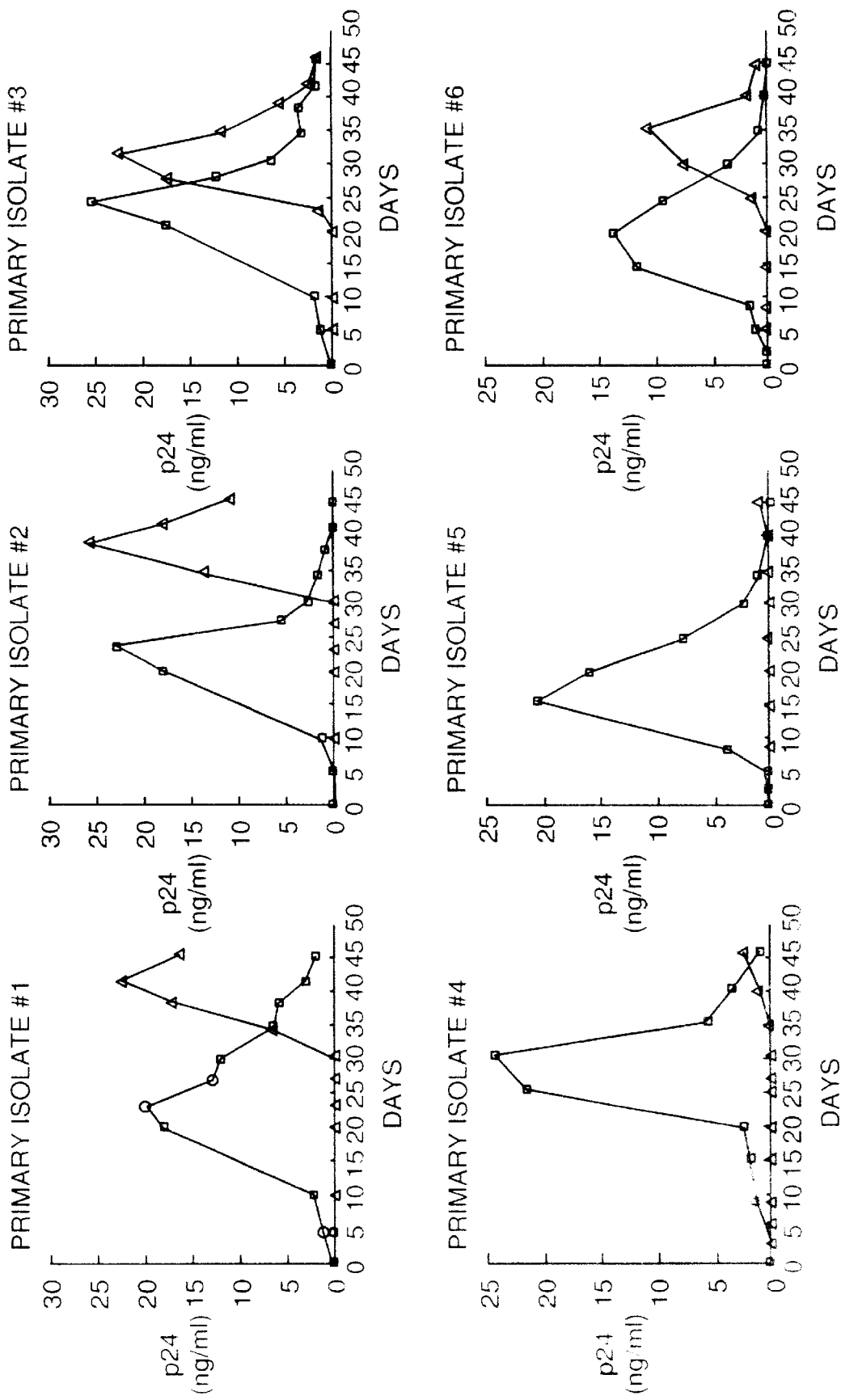
FIG. 3 shows resistance of stably transfected SupT-sFitat1Ck cells infected with HIV-1 with syncytium-inducing (SI)-primary isolates. Stably transfected SupT1-sFvtat1Ck and SupT-vector cells were challenged, in parallel, with six different European SI-primary isolates (FIGS. 3A–3F) (20ng/ml p24). Squares, SupT-vector cells; triangles, SupT-sFvtat1Ck cells. The cell free supernatant samples obtained on different days post-infection were processed as described in FIGS. 2A and 23.

The SupT-sFvtat1Ck and SutpT-vector cells were next challenged with six different SI-primary isolates at a fixed challenge dose of HIV-1 (20 ng p24/ml). As shown in FIG. 3, infections of SupT-vector cells with all six SI-primary isolates resulted in p24 detection by day 5 and reached a peak at day 15–20. In contrast, the SupT-sFvtat1Ck cells were protected to varying degrees but in all cases, a marked delay in p24 production was noted. With primary isolates #4 and #5, there was a delay of circa 40–45 days before p24 production was observed.
Resistance of Persistently Infected and Stably Transfected U 1 Pro-Monocytic Cells to Production of HIV-1

The persistently infected U 1 pro-monocytic cell line contains two copies of HIV-1 proviral DNA and can be induced by PMA and TNFα to upregulate HIV-1 mRNA synthesis[21,40,41]. This cell line serves as a model for latent infection and cytokine-inducible HIV-1-replication. Recent reports have established that a reservoir of latently infected cells persists in HIV-1-infected patients that have clinically responded to highly active anti-retroviral therapy (HAART)[42,43].

Figure 4A:
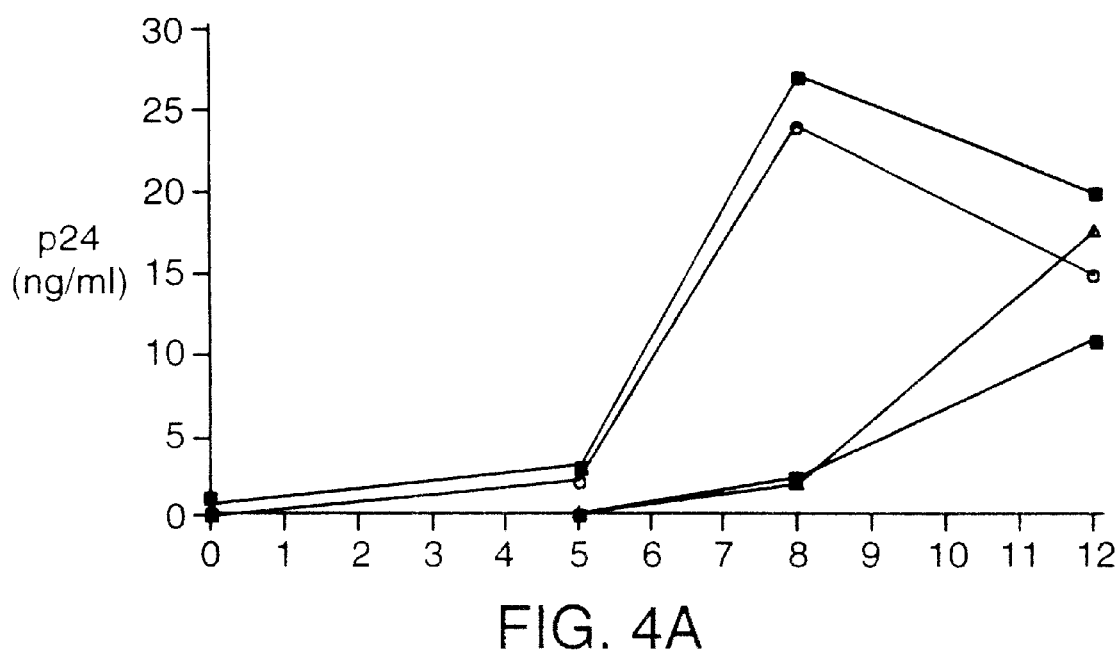
FIGS. 4A and 4B show resistance of stably transfected U1 pro-monocytic cells to production of HIV-1. Bulk stably transfected or parental cells were treated with 5ng/ml of PMA (FIG. 4A) or 5 mg/ml of TNFα (FIG. 4B) and cell-free supernatants were harvested for analysis of p24 levels. Circles, U1-vector cells; asterisks, U1-sFvTac cells; closed squares, U1-sFvtat1 cells; triangles, U1-sFvtat1Ck cells.
Figure 4B:
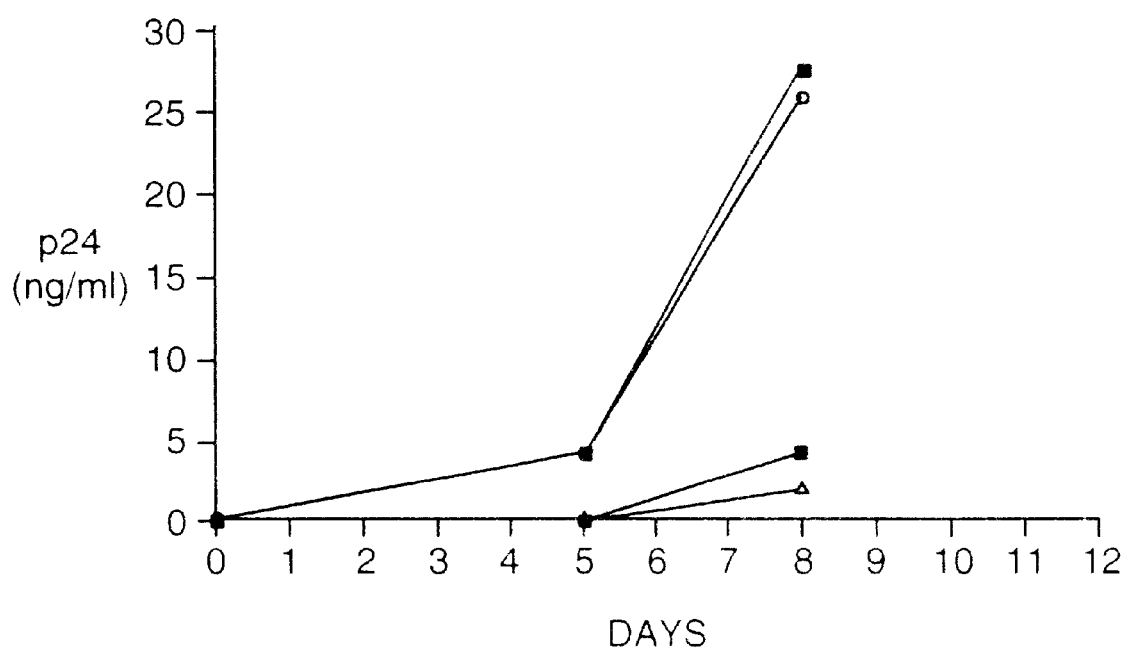
Figure 5A:
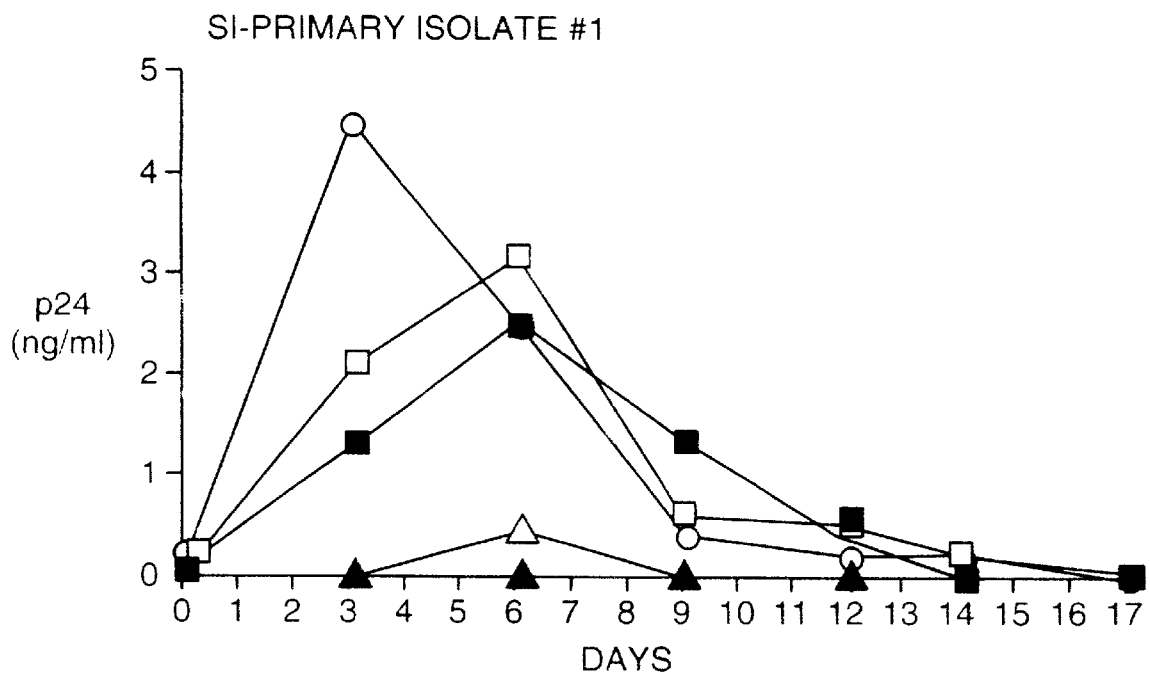
FIGS. 5A–5F show resistance of selected and total bulk populations of transduced CD4+ PBMCs to HIV-1-infection. CD4+-selected (FIGS. 5A, 5B), CD8+-depleted (FIGS. 5C, 5D) and total PBMCs (FIGS. 5E, 5F) were transduced with retrovirus containing supernatants from one or more PG 13 packaging cell lines expressing empty vector (circles), or vectors expressing sFvtat1(open and closed squares) or sFvtat1Ck (open and closed triangles). Transduced cells were selected for G418 (800 μg/ml) resistance and bulk populations of cells were challenged with 0.1 m.o.i. of either SI-primary isolate #1 (upper panels) or SI-primary isolate #2 (lower panels). Cell-free supernatants were harvested for analysis of p24 levels.
Figure 5B:
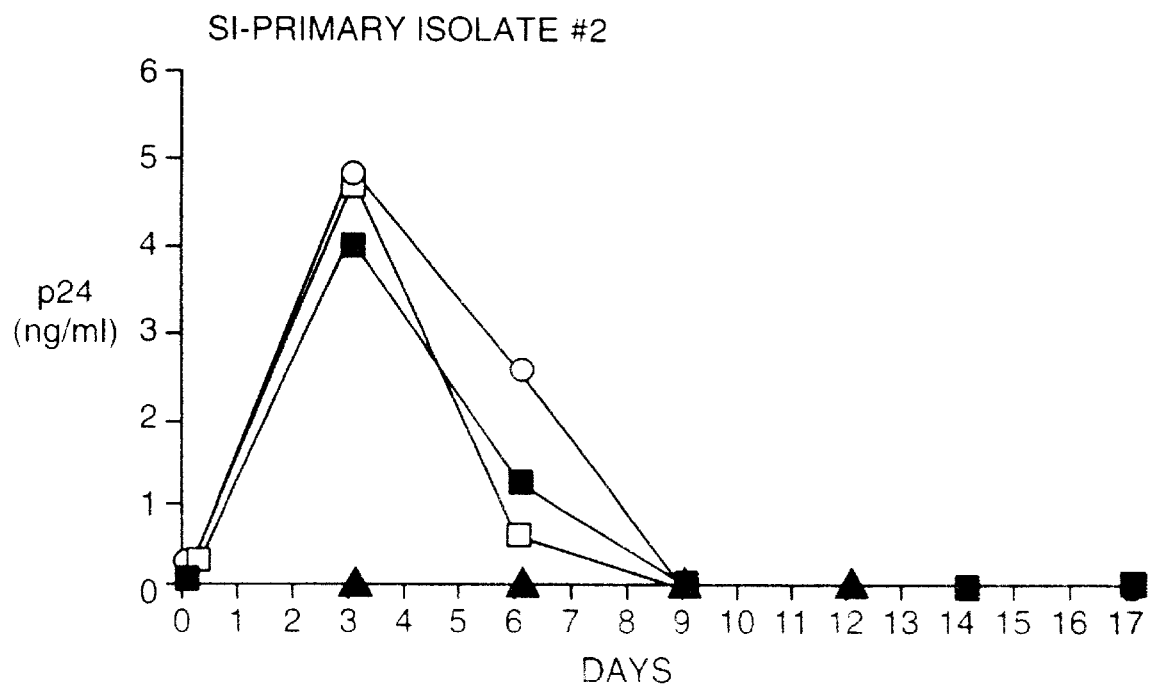
Figure 5C:
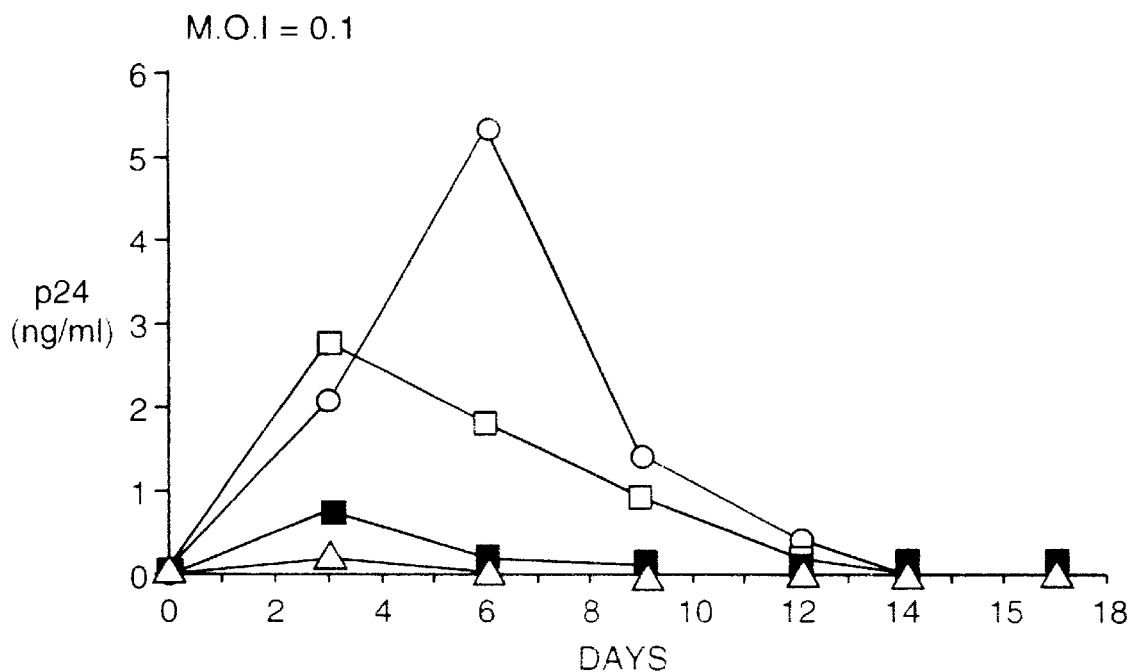
Figure 5D:
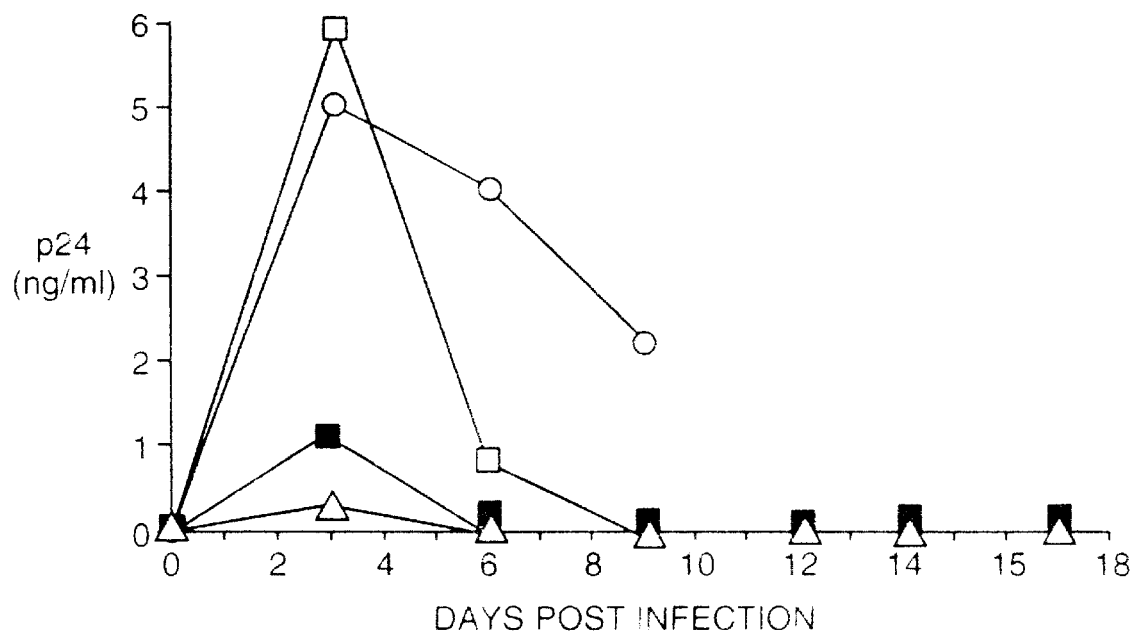
Figure 5E:
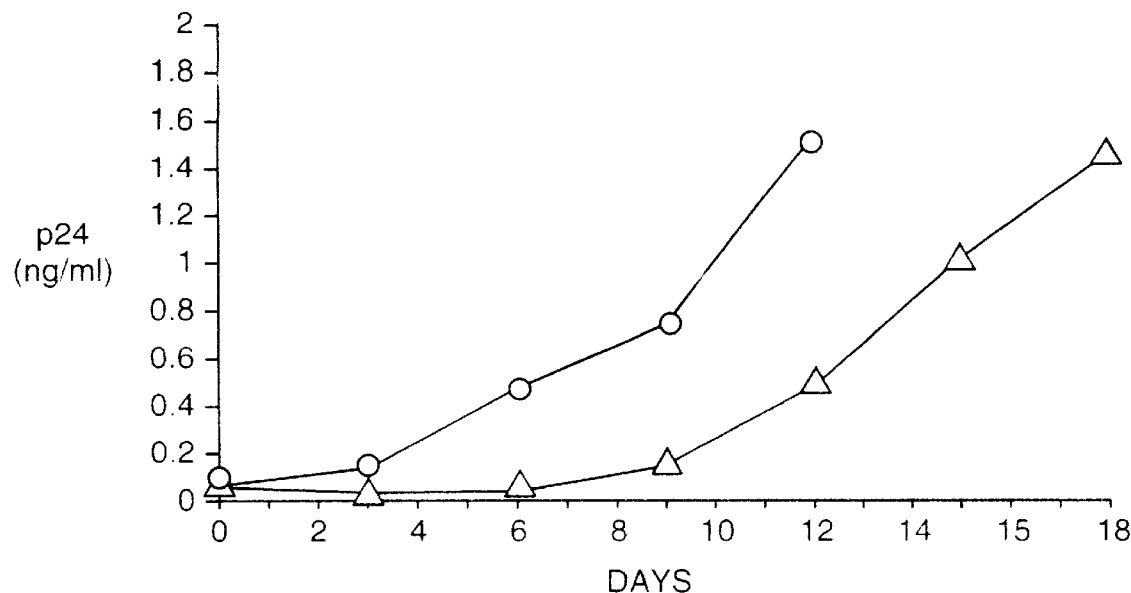
Figure 5F:
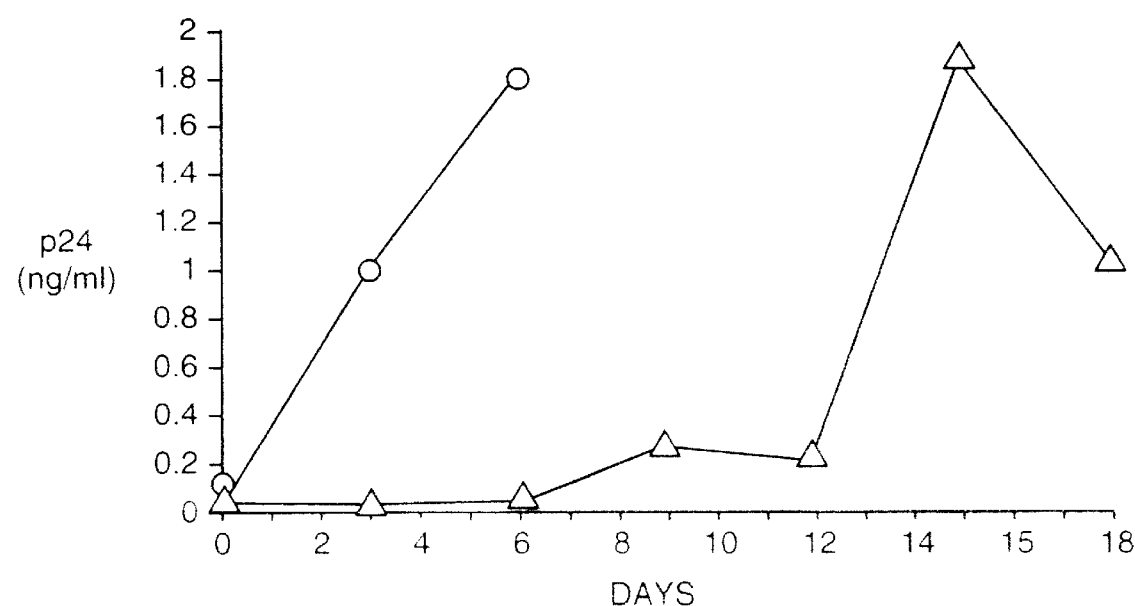

Bulk populations of stably transfected U1-sFvtat1, U1-sFvtat1Ck, U1-sFvTac and U 1-vector cells were treated with different concentrations of PMA and TNFα and cell free supernatants were harvested on alternate days and analyzed for p24 levels. As shown in FIG. 4A the PMA stimulated sFvtat I and sFvtat1Ck expressing U1 cells showed a reduction and delay in p24 production at eight days post-stimulation with 5 ng/ml PMA compared to irrelevant sPvTac expressing cells or vector cells. However, by 12 days poststimulation this reduction in p24 production was no longer observed. When cells were stimulated with 1 ng/ml TNFα, a marked reduction in p24 production was seen over the eight day experiment (FIG. 4B). At higher concentrations of PMA (10 ng/ml) and TNFα (10 ng/ml), neither a delay nor a reduction in p24 production was seen (data not shown). Thus under some conditions of stimulation, latently infected U 1 cells expressing anti-tat sFv intrabodies can be protected against activation of latent HIV-1.
HIV-1 Challenge of Retrovirally Transduced Human PBMCs Expressing sFvtat 1 Ck HIV-1 challenge experiments with two SI-primary isolates were carried out on G418 resistant bulk populations of CD4⁺-selected and CD8⁺-depleted peripheral blood mononuclear cells as well as on total PBMCs. In these studies, cells were transduced with retroviral supernatants from one or two different PG13 packaging cell lines producing either empty vector expressing only the neo selection marker or vectors expressing the sFvtat1or sFvtat1Ck intrabodies. As shown in FIG. 5, the transduced CD4⁺-selected (FIGS. 5A and.5B) and CD8⁺-depleted (FIG. 5C and 5D) peripheral blood mononuclear cells expressing the sFvtat1Ck intrabody showed marked resistance to infection with both SI-primary isolates when challenged at a m.o.i.=0.1. In contrast, the sFvtat 1 intrabody expressing cells have only a small inhibitory effect on HIV-1 production in agreement with our previous reports (FIGS. 5A–5D) HIV-1 challenge of transduced PBMCs (FIGS. 5E and 5F) showed greater protection against primary isolate #2 than against primary isolate #1.

Transduced PBMCs expressing sFvtat1Ck were also tested for surface phenotype by FACS analysis. As shown in FIG. 6, the murine sFrtat1Ck expressing PBMCs were unaffected by the intracellularly expressed sFvtat1Ck in their expression of a large number of cell surface molecules.
Inhibition of HIV-1 Replication in Transduced PBMCs Expressing Humanized Anti-tat sFv Intrabodies.

The primary amino acid sequences of the murine anti-tat heavy and light variable region genes were compared to 1238 heavy and 1041 light human variable immunoglobulin genes, respectively. "Best matched" human $V_H$ and $V_L$ sequences for anti-tat were chosen on the basis of high overall framework matching, similar CDR length, and minimal mismatching of canonical and $V_H/V_L$ contact residues. Based on these criteria, human immunoglobulin genes K5B8 and TR1.6 were chosen for framework humanization (FIGS. 1 and 7). Three different versions of humanized anti-tat were constructed. sFvhutat2 contained strictly human framework residues, while sFvhutat1 retained five murine amino acids at framework positions and sFvhutat3 retrained one murine amino acid.

Transduced and G418 selected bulk populations of PBMCs expressing empty vector, murine sFvtat1Ck or the humanized sFvhutat1, sFhutat2, sFvhutat2Ck or sFvhutat3 intrabodies were challenged with HxB2 and SI-primary isolates #1 and #2. As shown in FIG. 8, cells transduced with empty vector, sFvhutat1 or sFvhutat3 were similar in susceptibility to HIV-1 infection, with high levels of cell free p24 being observed as early as 3–5 days post-challenge with the laboratory strain and two SI-primary isolates. In contrast, cells transduced with murine sFvtat1Ck and the humanized sFvhutat2 and sFvhutat2Ck were resistant to HIV-1 infection and showed similar efficacy at protecting the cells as long as 17–21 days after viral challenge. Of interest and in contrast to our results with murine sFvtat1 (Mhashilkar[37] and FIGS. 5A&B), sFvhutat2 appears to be equal or slightly better than sFvhutat2 Ck in inhibiting HIV-1 replication.
Effects of transduction on cell surface receptor expression.

Transduced peripheral blood lymphocytes were grown in vitro for 4 weeks and assayed for frequency of CD4 cells. Cells were labeled with a mouse anti-human CD4 antibody followed by a FITC labeled goat anti-mouse $F(ab)_2$-antibody. Cells were counted in a fluorescence microscope.

This was done to determine if the transduction protocol will affect the distribution/frequency of $CD4^+$ T-cells that is the main target population of HIV-1 gene therapy. There was no apparent change in the frequency and level of CD4 expression.

CD4 expression in single-chain antibody transduced human PBMC's

| CD4 expression in single-chain antibody transduced human PBMC's | |
| --- | --- |
| Retroviral Vectors | % Pos. Cells |
| LNCX | 47.1 |
| LN-sFvhutat2 | 46.2 |
| LN-sFvhutat2Ck | 50.0 |
| No Vector | 50.0 |

METHOD OF USING sFvhatat2 IN INTRACELLULAR TARGETTING
Generation of LN-hsFvtat Packaging Cell Lines A method which has previously been used to successfully generate high titer retroviruses involves initially transfecting an ecotropic packaging call line, such as PE501, with the therapeutic vector construct containing the sFvhutat2 antibody (see FIG. 7). Virions produced by this packaging cell line are species-specific, and can only infect murine-derived cell populations. Retrovirus-containing supernatant is collected form the transfected PE501 packaging cell line, and used to infect an amphotropic cell line, such as PG13. Retroviral particles produced by PG13 possess a broad host range, and are thus capable of infecting a cell from a variety of species, including humans. The LN-sFvhutat vector is initially transfected into the PE501 packaging cell line, followed by infection of the PG13 packaging cell line with PE501 retroviral supernatants. The PG13 cells are exposed to this virus-containing media for 24 hours, in the presence of 8 μg/ml protamine sulfate (SIGMA). Two days after infection, the PG13 cells are subjected to selection in 800 μg/ml G418, which positively selects for the neomycin phosphotransferase gene product, whose expression is driven by the LN retroviral LTR promoter. Individual cones are then tested for production of high-titer retrovirus, by titering PG13 supernatants on COS-1 cells, using G418 selection to screen for effective gene transfer. Both the PE501 and PG13 cell lines are derived from NIH/3T3 thymidine kinase-negative cells, a marker which enables the positive selection of packaging-competent cells.

The PE501 and PG13 packaging cell lines were provided by the Fred Hutchinson Cancer Research Center, Seattle, Wash. These cell lines have been extensively described in other RAC-approved gene therapy protocols. We have isolated clones producing retroviral titers in the order of $10^6$PFU/ml, as measured on COS-1 cells. The S+L-assay is used for detection of replication competent virus in virus supernatants following amplification on 3T3 cells. Before utilization in human studies, the cells are certified to be free of contaminating replication competent retrovirus and other adventitious agents by criteria recommended by the FDA. All batches of the LNCX (empty vector) and LN-hsFvtat producer cell lines tested in humans will have met FDA specifications for current clinical human gene therapy trials in progress. For example, clinical grade vectors from either Magenta Corporation or the National Gene Vector Laboratory (NGVL) of Dr. Ken Cornetta. The NGVL is an NIH Resource sponsored by the National Center for Research Resources, the National Cancer Institute, the National Heart, Lung, and Blood Institute, and the National Institute of Diabetes and Digestive and Kidney Diseases.
Previous Human Gene Therapy Trials for AIDS In 1990, the first human.gene therapy trial was started using retroviral-mediated transfer of the adenosine deaminase (ADA) gene into the T cells of two children with severe combined immunodeficiency (SCID). Although the trial was ended after two years, four years after the beginning of the trial circulating T cells expressing the ADA gene could still be detected. This gene therapy trial was concluded to be both safe and effective as a treatment alternative for SCID caused by a defective ADA gene.

Since 1990, a number of other gene therapy protocols have begun phase I safety trials. One such AIDS gene therapy study involves the retroviral-mediated transfer of a vector construct encoding a transdominant negative form of the HIV-1 rev protein (Rev M10). When tested in SCID mice for tumorigenicity prior to clinical trial itself, the Rev M10 construct failed to induce oncogenicity. Preliminary clinical results from that study indicate this modality of gene transfer to be both safe and non-toxic. Furthermore, these preliminary data also demonstrate that Rev M10-transduced cells show preferential survival compared to ΔRev10 (frameshift) control cells.
Patient Selection Patients with Human Immunodeficiency Virus-1 (HIV-1) infection will be enrolled. The patients will see their usual care giver throughout the study, with whom ongoing communication will be established by the trial investigators. The period of surveillance is one year.
A. Inclusion Criteria
 (1) HIV-1 infection as documented by any licensed ELISA test kit and confirmed by either Western blot, HIV culture, HIV antigen, plasma HIV RNA or a second antibody test by a method other than ELISA at any time prior to study entry.
 (2) A CD4 cell count>100 cells/mm3within 30 days prior to study entry.
 (3) Plasma HIV RNA>10,000 copies/ml within 30 days prior to study entry.
 (4) Patients should be on a stable antiviral therapy regimen for at least six weeks prior to cell harvesting for the purpose of this trial. It is understood that therapy intolerance (resulting from toxicities including, but not limited to, bone marrow suppression, intractable nausea, myopathy) could occur during the study in any given patient and may necessitate withdrawals of the drug.

(5) Patient CD8-depleted PBMC transducibility>5% as determined by ex-vivo transduction and confirmed by PCR.
(6) Adequate hepatic function:
e.g., bilirubin<1.5 mg$^2$, SGOT<60 i$\mu$.
(7) Adequate renal function:
BUN<20 mg$^2$, Serum creatinine<1.5 mg/dl.
(8) Adequate bone marrow function:
e.g., WBC>4000/mm$^2$, Platelets>100,000/mm$^2$.
(9) Age$\geq$18 and$\leq$physiological 65 years.
  (a) Patients of either sex are eligible. Preferably patients with reproductive potential, male or female, will agree to use an effective method of contraception during the study period. Female subjects should have a negative serum pregnancy test.
  (b) Karnofsky score>80% at enrollment.
(10) the patient must be able to provide informed consent.

B. In this situation, it is preferable to initially exclude patients having the following criteria. However, these patient can be treated by use of the present antibody.
(1) Laboratory parameters:
  (a) CD4$^+$cell count<100/mm$^3$
  (b) Hematocrit <30%
  (c) Platelet count <100,000/mm$^3$
  (d) White blood cell count <4000/mm$^3$
  (e) Absolute neutrophil count <1000/mm$^3$
  (f) Creatinine>1.5 mg/dl
  (g) Total bilirubin >1.5 mg/dl
  (h) SGOT >60 i$\mu$
  (i) CD8-depleted PBMC transducibility <5%
  (j) Plasma HIV RNA <10,000 copies/ml
(2) Ongoing AIDS-defining opportunistic infections or malignancies (see Appendix B and C). Where previous opportunistic infections have occurred, a 30-day period following full recovery is required.
(3) Acute therapy for an infection or other medical illness within 14 days prior to study entry.
(4) Unexplained temperature >38.5° C. for any 7 days, or chronic diarrhea defined as >three liquid stools per day persisting for 15 days, within 30 days prior to study entry.
(5) A malignancy which requires systemic chemotherapy.
(6) Proven suspected acute hepatitis within 30 days prior to study entry, even if AST (SGOT) and ALT (SGPT) are<5.0×ULN.
(7) Taking the following medications:
  (a) Interferons, interleukins, GM-CSF, or HIV vaccines within 30 days prior to study entry.
  (b) Any experimental therapy (drugs or vaccines) within 30 days prior to study entry.
  (c) Rifampin or rifabutin within 14 days prior to study entry.
  (d) Systemic cytoxic chemotherapy within 30 days prior to study entry.
(8) Pregnant or nursing women.
(9) Any other serious chronic illness including, but not limited to: diabetes, chronic active hepatitis, sarcoidosis, active autoimmune disease (such as rheumatoid arthritis, systemic lupus erythematosus, Reiter's Syndrome, inflammatory bowel disease, thyroiditis, etc.), coronary artery disease, cardiomyopathy, chronic obstructive pulmonary disease, dementia.
(10) Patients receiving systemic glucocorticosteroids.
(11) Allergy to penicillin and synthetic derivatives, streptomycin or amphotericin B.
(12) Active alcohol or drug abuse, or other psychiatric impairment that in the view of the investigators would impair participation in the trial.
(13) Any occupational or personal circumstances which, in the opinion of the investigators, would prevent compliance with the protocol.
(14) Patients who have undergone alternative non-FDA approved treatment within 30 days prior to study entry.

A. Gene Transfer Methods

In the gene transfer protocol outlined below, measures will be employed to avoid activation of any latent HIV-1 present in the patients' peripheral blood lymphocytes. The non-nucleoside reverse transcriptase (RT) inhibitor nevirapine will be included during the ex vivo expansion and transduction of patient lymphocytes for patients who have not previously received this agent. Nevirapine belongs to the class of non-nucleoside RT inhibitors, a group of structurally diverse compounds which noncompetitively inhibit HIV-1 RT and viral replication at nM concentrations, with typical therapeutic indices of 1,000 to 1 (as assayed in cultured cells). These non-nucleoside RT inhibitors are highly specific for HIV-1, lacking any activity against HIV-2, SIV, or any other retroviral source of reverse transcriptase. In order to ensure the efficaciousness of this therapeutic regimen in suppressing activation of latent HIV-1, we will also test the expanded cell populations for HIV-1 gag expression, using the highly sensitive (pg/ml range) HIV-1 p24 antigen capture assay (DuPont-NEN).

For nevirapine-experienced patients, other in vitro drug regimens will be employed to suppress viral activation. The choice of these regimens will depend on the patient's previous drug experience, i.e., agents will be selected to which the patient has not had previous exposure.

(1) Drug Formulation and Procurement
(a) Harvesting of Patient PBMCs for Ex Vivo Stimulation A chain of purity and sterility will be maintained and documented through the study. Since the procedures of cell procurement, purification, activation, transduction, and expansion together will take approximately two to three weeks, we will perform our studies on one patient at a time, at approximately one month intervals.

Following completion of baseline acquisition, subjects will undergo one cycle of lymphophoresis at for example, the DFCI (Dana-Farber Cancer Institute, Inc.) blood bank, or other designated clinical facility. Fresh peripheral blood mononuclear cells (PBMCs) will be separated from erythrocytes and neutrophils by Ficoll-Hypaque density gradient centrifugation. After being washed, the PBMCs will be depleted of CD8$^+$, cells using murine anti-human CD8$^+$ monoclonal antibody-coated magnetic beads (Dynal). The beads will be mixed with the cells and incubated at 2–4° C. for approximately one hour, while gently mixing. After incubation, a magnet will be apposed to the tube outside wall. Those cells expressing the CD8 receptor will bind the monoclonal antibody affixed to the beads, and will therefore remain inside the tube. Thus, only CD8$^+$, cells will be poured into the new culture vessel, yielding a CD8-depleted population.

The CD8-depleted cell. population will then be stimulated in CM [CM=AIM-V serum free medium (Gibco) with 2 mM glutamine, 100 U/ml penicillin, 100 $\mu$g/ml streptomycin, 50–1,000 U/ml IL-2 (depending on patient PBMC in vitro growth response), and 10 $\mu$g/ml of the HIV-1 non-nucleoside RT inhibitor, nevirapine (Boerhinger-Ingelheim)] with 50 ng/ml of both OKT3 and soluble anti-CD28 monoclonal antibodies. Cellular phenotype will be assessed by flow cytometry prior to the expansion protocol described.

(b) Transduction of CD8-depleted PBMCs

Following activation, the cells will be resuspended at $1-2\times10^6$ cells/ml in complete fresh CM containing 20–100 U/mnl IL-2 (Collaborative Research, Bedford, Mass.). Two identical aliquots of cells will be transduced simultaneously, one with the LN-sFvhutat construct, the other will the LN control vector only (vector lacking the sFvhutat2 cassette). Frozen viral supernatant will be stored at $-80°$ C. On the day of transduction, aliquots will be thawed and passed through a 0.45 mm filter. The cells will then be washed and subsequently transduced.

Transduction will be performed by adding to the culture medium an equal volume of viral supernatant (MOI of 1), supplemented with protamine sulfate at a final concentration of 8 µg/ml, as well as 20–100 U/ml of IL-2. The cells will then be centrifuged at 2,600 rpm for one hour at room temperature, followed by an overnight incubation at 37° C. The next day, the cells will be washed in supplemented AIM-V CM, and the transduction protocol will be repeated as described. This protocol will then be repeated a third and final time using identical conditions, after which the cells will be washed. three times in CM, and introduced into tissue culture bags. At this stage, the cells will be ready to undergo the large scale expansion required for therapy.

(c) Expansion of transduced PBMCs

Transduced lymphocytes, resuspended at $1-2\times10^5$ cells/ml in complete fresh CM containing 50–1,000 U/ml of IL-2 (patient-dependent), will be expanded using 50 ng/ml OKT3and 50 ng/ml anti-CD28 in 3,000 ml culture bags each containing about 500–1,000 ml media. Cells are grown to maximum density (about $2-5\times10^6$ cells/ml). Expansion is estimated to take 1–2 weeks. Administration of nevirapine (or other anti-viral medications) to the culture will be terminated just prior to completion of the expansion procedure. Subsequent cell washes will prevent significant carry-over of these agents into the patient. A p24 antigen capture assay will preferably be performed at completion of this stage. However, testing of the final cell pellet prior to re-infusion may not be possible in all cases.

(2) Description of Treatment Protocol (a) Infusion of Transduced, Expanded Autologous Lymphocytes The transduced cells will be harvested, washed, and resuspended in sterile PBS. The final cell preparation will be filtered through a platelet filter and transferred into a syringe or transfusion pack for infusion. Interim history and physical examination will be performed by an investigating physician. Intravenous cathertization with standard sterile technique will be performed and good venous return and absence of infiltration will be verified immediately before infusion.

The infusions will be performed. The optimal target cell number for infusion will be no less than $5\times10^8$ cells/kg and no more than $1\times10^9$ cells/kg of body weight (The does target per infusion in the ADA Clinical protocol was $1-3\times10^9$ per kg). The total volume of infused cells should not exceed 10 ml/kg of body weight.

After an initial test infusion of 1–5% of the total volume, cells will be infused over the next 60–120 minutes. During infusion, the cell suspension will be mixed gently approximately every 5 minutes while the patient is being observed for acute and subacute toxicity. Vital signs will be monitored before infusion and every 15 minutes during and 2 hours after infusion or until the patient is stable. The infusion will be terminated if systolic blood pressure falls below 80 mm Hg, oxygen saturation falls below 90%, or other evidence of major systemic toxicity occurs. Patients will have nursing observation for 24 hours after infusion; patients will be discharged after 24 hours if there are no complications. A blood sample or samples will be drawn prior to discharge.

REFERENCES

1. A. Dayton et al., *Cell* 44:41–947 (1986).
2. A. Fisher et al., *Nature* 320:367–371 (1986).
3. S. Kao et al., *Nature* 330:489–493 (1987).
4. M. Laspia et al., *Cell* 59:283–292 (1989).
5. M. Feinberg et al., *Proc. Natl. Acad. Sci. USA* 88:4045–4049 (1991).
6. L. Huang et al., *EMBO J.* 13:2886–2896 (1994).
7. D. Harrich et al., *EMBO J.* 16:1224–1235 (1997).
8. C. Cupp et al., *Oncogene* 8:2231–2236 (1993).
9. R. Viscidi et al., *Science* 246:1606–1608 (1989).
10. T. Howcroft et al., *Science* 260:1320–1322 (1993).
11. C. Li et al., *Proc. Natl. Acad. Sci. USA* 92:5461–5464 (1995).
12. M. Westendorp et al., *EMBO J.* 14:546–554 (1995).
13. K. Sastry et al., *J. Biol. Chem.* 265:20091–20093 (1990).
14. L. Buonaguro et al., *J. Virol.* 66:7159–7167 (1992).
15. L. Buonaguro et al., *J. Virol.* 68:2677–2682 (1994).
16. K. Nakajima et al., *J Immunol.* 142:531 (1989).
17. G. Scala et al., *J. Exp. Med.* 179:961–971 (1994).
18. E. Duh et al., *Proc. Natl. Acad. Sci. USA* 86:5974–5978 (1989).
19. G. Poli et al., *J. Exp. Med.* 172:151–158 (1990a).
20. G. Poli et al., *Proc. Natl. Acad. Sci. USA* 87:782–785 (1990b).
21. W. Popik et al., *J. Virol.* 67:1094–1099 (1993).
22. M. Westendorp et al., *J. Virol.* 68:4177–4185 (1994).
23. M. Ott et al., *Science* 275:1481–1485 (1997).
24. C. Li et al., *Proc. Natl. Acad. Sci. USA* 94:8116–8120 (1997).
25. G. Goldstein, *Nature Med.* 1:960–964 (1996).
26. R. Haubrich et al., *J. Infect. Dis.* 172:1246–1252 (1995).
27. M. Hsu et al., *Proc. Natl. Acad. Sc. USA* 90:6395–6399 (1993).
28. B. Sullenger et al., *Cell* 63:601–608 (1990).
29. H. Chang et al., *Gene Therapy* 1:208–216 (1994).
30. C. Zhou et al., *Gene* 149:33–39 (1994).
31. E. Aguilar-Cordova et al., *Gene Ther.* 2:181–186 (1995).
32. T. Vandendiiessche et al., *J. Virol.* 69:4045–4052 (1995).
33. J. Liszie,,icz et al., *Gene Ther.* 7:2209–2216 (1996).
34. M. Rosenzweig et al., *J Virol.* 71:2740–2746 (1997).
35. D. Biswas et al., *Proc. Natl. Acad. Sci. USA* 90:11044–11048 (1993).
36. A. Mhashilkar et al., *J Virol.* 71:6486–6494 (1997).
37. A. MhashiLlcar et al., *EMBO J* 14:1542–1551 (1995).
38. M. Poznansky et al., *Human Gene Ther.,* (1998), in press.
39. S. Riddell et al., *Nature Med.* 2:216–223 (1996)..
40. T. Folks et al., *Science* 238:800–802 (1987).
41. T. Folks et al., *J. Immunol.* 140:1117–1122 (1988).
42. J. Wonget al., *Science* 278:1291–1295 (1997).
43. D. Finzi et al., *Science* 278:1295–1300 (1997).
44. A. Goldberg et al., *Science* 268:522–523 (1995).
45. K. Rock et al., *Immunology Today* 17:131–137 (1996).
46. M. Brenner et al.. *The Lancet* 341:85–86 (1993a).
47. M. Brenner et al., *The Lancet* 342:1134–1137 (1993b).
48. C. Bordignon et al., *Science* 270:470–475 (1995).
49. R. Blaese et al., *Science* 270:475–480 (1995).
50. C. Woffendin et al., *Proc. Nati. Acad. Sci. USA* 93:2889–2894 (1996).
51. C. Carpenter et al., *JAMA* 277:1962–1969 (1997).
52. R. Gulick et al., Indinavir (IDV), zidovudine (ZDV) and larnivudine (3TC); concurrent or sequential therapy in ZDV-experienced patients; 37th ICAAC, Toronto, Canada, Sept. 28–Oct. 1, 1997. Abstract I-89

53. S. Deeks et al.,Incidence and predictors of virologic failure to indinavir (IDV) or/and ritonavir (RTV) in an urban health clinic; 37th ICAAC, Toronto, Canada, Sept. 28–Oct. 1, 1997, Abstract LB-2.
54. J. Vogel et al., *Nature* 335:606–611 (1988).
55. B. Ensoli et al., *Nature* 371:674–680 (1994).
56. A. Albini et al., *Nature.Med.* 2:1371 (1996).
57. S. Mitola et al., *Blood* 90:1365–1372 (1997).
58. S. Dhawan et al., *Blood* 90:1535–1544 (1997).
59. W. Ho et al., *J of Gem Virol.* 71:97–103 (1990).
60. H. Tada et al., *Proc. Natl. Acad. Sci. USA* 87:3479–3483 (1990).
61. L. Sieczkowski et al., *Virology* 211:544–553 (1995).
62. V. Johnson et al., Techniques in HIV Research, Stockton Press, Stockholm, N.Y., pp 71–96 (1990).
63. A. Miller, Central Topics in Microbiology and Immunology. 158 (1991).
64. B. Bunnell et al., *Proc. Natl. Acad. Sci.* 92:7739–7743 (1995).
65. R. Morgan et al., *Human Gene Ther.* 1:135–149 (1990).
66. K. Jayararnan et al., *Proc. Natl. Acad. Sci. USA* 88:4084–4088 (1991).
67. R. Blaese et al., *Science* 270:475–479 (1995).
68. C. Bordignon et al., *Science* 270:470–475 (1995).
69. B. Fox et al., *Hum. Gene Ther,* 6:997–1004 (1995).
70. C. Woffendin et al., *Proc. Natl. Acad. Sci., USA,* 2:2889–2894 (1996).
71. M. Johnson et al., *Science* 260:1286–1293 (1993).
72. E. De Clercq, *Medicinal Research Reviews,* 13:229–258 (1993).
73. P. Grob et al., *AIDS Res and Hum Retrou,* 8:145–152 (1992).
74. K. Cornetta, *J Virol Methods* 23:187–194 (1989).

All of the references. cited herein are incorporated herein by reference.

What is claimed:

1. A. humanized antibody framework motif wherein said framework has been selected from a human library based upon comparison to a murine antibody, and the heavy chain is encoded by the $V_H$ gene of K5B8, and the light chain is encoded by the $V_L$ gene of TR1.6

2. The humanized antibody framework motif of claim 1, wherein no murine amino acid residue has been retained.

3. The humanized antibody framework motif of claim 1, wherein one to four of the five murine amino acid residues at the FRM2/CDR2 border and the FRM3/CDR3 border of the heavy chain is retained.

4. A humanized antibody framework motif of claim 1, wherein one to four of the murine amino acid within the FRM3 sequence of the light chain is retained.

5. The humanized antibody framework motif of claim 3, wherein one to four of the murine amino acid within the FRM3 sequence of the light chain is retained.

6. The humanized antibody framework motif of claim 3, wherein all said murine amino acid residues at the FRM2/CDR2 and the FRM3/CDR3 border of the heavy chain are retained.

7. The humanized antibody framework motif of claim 4, wherein all of said murine amino acid residues at the FRM2/CDR2 and the FRM3/CDR3 border of the heavy chain are retained.

8. The humanized antibody framework motif of claim 5, wherein all of said murine amino acid residues at the FRM2/CDR2 and the FRM3/CDR3 border of the heavy chain are retained.

9. The humanized antibody of claim 1, wherein the variable region is from an antibody to HIV tat.

10. The humanized antibody of claim 2, wherein the variable region is from an antibody to HIV tat.

11. The humanized antibody of claim 3, wherein the variable region is from an antibody to HIV tat.

12. The humanized antibody of claim 9, wherein the leader sequence is not present.

13. The humanized antibody of claim 11, wherein the leader sequence is not present.

14. The humanized antibody of claim 12, wherein a nuclear localization signal is present.

15. The humanized antibody of claim 12, wherein a nuclear localization signal is present.

16. A method of targeting a tat antigen intracellularly which comprises transfecting a cell with a gene encoding the antibody of claim 1, operably linked to a promoter.

17. A method of targeting a tat antigen intracellularly which comprises transfecting a cell with a gene encoding the antibody of claim 2, operably linked to a promoter.

18. A method of targeting a tat antigen intracellularly which comprises transfecting a cell with a gene encoding the antibody of claim 3, operably linked to a prompter.

19. The method of targeting a tat antigen intracellularly of claim 16, wherein the leader sequence is not present and wherein the variable region is from an antibody to HIV tat.

20. The method of targeting a tat antigen intracellularly of claim 17, wherein the leader sequence is not present and wherein the variable region is from an antibody to HIV tat.

21. The method of targeting a tat antigen intracellularly of claim 18, wherein the leader sequence is not present and wherein the variable region is from an antibody to HIV tat.

22. A method of targeting a tat antigen intracellularly which comprises transfecting a cell with a gene encoding the antibody of claim 14, operably linked to a promoter.

23. A method of targeting a tat antigen intracellularly which comprises transfecting a cell with a gene encoding the antibody of claim 15, operably linked to a promoter.

24. The humanized antibody framework motif of claim 4, wherein one murine amino acid within the FRM3 sequence of the light chain is retained, and said murine amino acid is either the first murine amino acid residue or the last murine amino acid residue within this region.

25. The humanized antibody framework motif of claim 5, wherein one murine amino acid within the FRM3 sequence of the light chain is retained and said murine amino acid is either the first murine amino acid residue or the last murine amino acid residue within this region.

26. The humanized antibody framework motif of claim 8, wherein one to four murine amino acid within the FRM3 sequence of the light chain is also present.

27. The humanized antibody framework motif of claim 4, wherein both the first murine amino acid residue. and the last amino acid residues with the FRM3 sequence of the light chain are retained.

28. The humanized antibody framework motif of claim 5, wherein both the first murine amino acid residue and the last amino acid residues with the FRM3 sequence of the light chain are retained.

29. The humanized antibody framework motif of claim 26, wherein both the first murine amino acid residue and the last amino acid residues with the FRM3 sequence of the light chain are retained.

30. The humanized antibody framework motif of claim 27, wherein the murine amino acid residue at the CDR3/FR4 boundary of the heavy chain is also retained.

31. The humanized antibody framework motif of claim 28, wherein the murine amino acid residue at the CDR3/FR4 boundary of the heavy chain is also retained.

32. The humanized antibody framework motif of claim 29, wherein the murine amino acid residue at the CDR3/FR4 boundary of the heavy chain is also retained.

* * * * *

UNITED STATES PATENT AND TRADEMARK OFFICE
CERTIFICATE OF CORRECTION

PATENT NO. : 6,479,284 B1
DATED : November 12, 2002
INVENTOR(S) : Marasco et al.

It is certified that error appears in the above-identified patent and that said Letters Patent is hereby corrected as shown below:

Column 27,
Line 36, delete "What is claimed" and insert -- SEQUENCE LISTINGS FOLLOWS --;
Line 38, insert the Sequence listings as shown on the attached sheets, to be followed by
-- What is claimed --.

Signed and Sealed this

Ninth Day of November, 2004

JON W. DUDAS
*Director of the United States Patent and Trademark Office*

SEQUENCE LISTING

<110> Dana-Farber Cancer Institute, Inc. et al.

<120> HUMANIZED ANTIBODIES AND USES THEREOF

<130> 700157-48085-C

<140> 09/660,169
<141> 2000-09-12

<150> PCT/US99/05262
<151> 1999-03-11

<150> 60/077,845
<151> 1998-03-13

<160> 6

<170> PatentIn version 3.1

<210> 1
<211> 117
<212> PRT
<213> Artificial Sequence

<220>
<223> Humanized sFvtat1

<400> 1

Gln Val Gln Leu Lys Gln Ser Gly Pro Gly Leu Val His Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Asn Ile Thr Lys Asp Asn Ser Lys Arg Gln Val Phe Phe
65                  70                  75                  80

Lys Met Asn Ser Leu Gln Ala Asp Asp Thr Ala Ile Tyr Tyr Cys Ala
            85                  90                  95

Arg Glu Pro Pro Thr Thr Tyr Val Cys Leu Leu Gly Gln Gly Thr Ser
            100                 105                 110

```
Val Thr Val Ser Ser
        115

<210>  2
<211>  119
<212>  PRT
<213>  Homo sapiens

<400>  2

Gln Val Gln Leu Lys Gln Ser Gly Pro Gly Leu Val His Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Met Trp Arg Gly Gly Ser Thr Asp Tyr Asn Ala Ala Phe Met
    50                  55                  60

Ser Arg Leu Asn Ile Thr Lys Asp Asn Ser Lys Arg Gln Val Phe Phe
65                  70                  75                  80

Lys Met Asn Ser Leu Gln Ala Asp Asp Thr Ala Ile Tyr Tyr Cys Ala
                85                  90                  95

Lys Ser Met Ile Thr Thr Gly Phe Val Met Asp Ser Trp Gly Gln Gly
                100                 105                 110

Thr Ser Val Thr Val Ser Ser
        115

<210>  3
<211>  114
<212>  PRT
<213>  Artificial Sequence

<220>
<223>  Humanized sFvtatl

<400>  3

Glu Leu Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Val His Ser
                20                  25              30
Asn Gly Ile Thr Tyr Leu His Trp Tyr Leu Gln Lys Pro Gly Gln Ser
            35              40              45
Pro Gln Leu Leu Ile Tyr Lys Val Ser Asn Arg Phe Ser Gly Phe Pro
        50              55              60
Asp Arg Phe Ser Gly Ser Gly Ser Gly Thr Asp Phe Thr Leu Lys Ile
65              70              75              80
Ser Arg Val Glu Ala Glu Asp Val Gly Val Tyr Phe Cys Ser Gln Ser
                85              90              95
Thr His Ile Pro Trp Thr Gly Gly Gln Gly Thr Lys Leu Glu Ile Lys
            100             105             110
Arg Ala

<210> 4
<211> 109
<212> PRT
<213> Homo sapiens

<400> 4
Glu Leu Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Gly
                20                  25              30
Asn Gly Tyr Asn Tyr Leu Asp Trp Tyr Leu Gln Lys Pro Gly Gln Ser
            35              40              45
Pro Gln Leu Leu Ile Tyr Leu Gly Ser Asn Arg Ala Ser Gly Val Pro
        50              55              60
Asp Arg Phe Ser Gly Ser Gly Ser Gly Thr Asp Phe Thr Leu Lys Ile
65              70              75              80
```

```
Ser Arg Val Glu Ala Glu Asp Val Gly Val Tyr Tyr Cys Met Gln Ala
                85                  90                  95

Leu Gln Pro Pro Tyr Thr Phe Gly Gln Gly Thr Lys Leu
            100                 105
```

<210> 5
<211> 117
<212> PRT
<213> Mus musculus

<400> 5

```
Pro Val Lys Leu Gln Glu Ser Gly Pro Gly Leu Val Ala Pro Ser Gln
1               5                   10                  15

Arg Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
            35                  40                  45

Val Val Ile Trp Ser Asp Gly Ser Thr Thr Tyr Asn Ser Ala Leu Lys
        50                  55                  60

Ser Arg Leu Asn Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Glu Pro Pro Thr Thr Tyr Val Cys Leu Leu Gly Gln Gly Thr Ser
            100                 105                 110

Val Thr Val Ser Ser
            115
```

<210> 6
<211> 114
<212> PRT
<213> Mus musculus

<400> 6

```
Glu Leu Val Leu Thr Gln Ser Pro Leu Ser Leu Pro Val Ser Leu Gly
1               5                   10                  15
```

```
Asp His Ala Ser Ile Ser Cys Arg Ser Ser Gln Ser Leu Val His Ser
            20              25              30

Asn Gly Ile Thr Tyr Leu His Trp Tyr Leu Gln Lys Pro Gly Gln Ser
            35              40              45

Pro Lys Leu Leu Ile Tyr Lys Val Ser Asn Arg Phe Ser Gly Phe Pro
    50              55              60

Asp Arg Phe Ser Gly Ser Gly Ser Gly Thr Asp Phe Thr Leu Lys Ile
65              70              75              80

Gly Arg Val Glu Ala Glu Asp Leu Gly Val Tyr Phe Cys Ser Gln Ser
                85              90              95

Thr His Ile Pro Trp Thr Phe Gly Gly Gly Thr Lys Leu Glu Ile Lys
            100             105             110

Arg Ala
```